US008889694B2

(12) United States Patent
Eckelbarger et al.

(10) Patent No.: US 8,889,694 B2
(45) Date of Patent: Nov. 18, 2014

(54) N-ALKOXYAMIDES OF 6-(SUBSTITUTED PHENYL)-4-AMINOPICOLINATES AND 2-(SUBSTITUTED PHENYL)-6-AMINO-4-PYRIMIDINE CARBOXYLATES AND THEIR USE AS SELECTIVE HERBICIDES FOR CROPS

(71) Applicants: Joseph D. Eckelbarger, Carmel, IN (US); Paul R. Schmitzer, Indianapolis, IN (US); Carla N. Yerkes, Crawfordsville, IN (US); Timothy A. Boebel, Indianapolis, IN (US); Norbert M. Satchivi, Carmel, IN (US); Gregory T. Whiteker, Carmel, IN (US)

(72) Inventors: Joseph D. Eckelbarger, Carmel, IN (US); Paul R. Schmitzer, Indianapolis, IN (US); Carla N. Yerkes, Crawfordsville, IN (US); Timothy A. Boebel, Indianapolis, IN (US); Norbert M. Satchivi, Carmel, IN (US); Gregory T. Whiteker, Carmel, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 13/962,333

(22) Filed: Aug. 8, 2013

(65) Prior Publication Data
US 2013/0324412 A1    Dec. 5, 2013

Related U.S. Application Data

(62) Division of application No. 12/712,483, filed on Feb. 25, 2010, now Pat. No. 8,536,331.

(60) Provisional application No. 61/156,088, filed on Feb. 27, 2009.

(51) Int. Cl.
*A01N 43/08* (2006.01)
*A01N 43/16* (2006.01)
*A01N 43/40* (2006.01)
*A01N 43/54* (2006.01)
*A01N 43/74* (2006.01)
*A01N 43/78* (2006.01)
*A01N 43/80* (2006.01)
*A01N 43/82* (2006.01)
*C07D 239/30* (2006.01)
*C07D 413/12* (2006.01)
*C07D 405/12* (2006.01)
*C07D 413/06* (2006.01)
*C07D 417/12* (2006.01)
*C07D 213/81* (2006.01)
*A01N 43/72* (2006.01)
*C07D 239/28* (2006.01)
*C07D 239/47* (2006.01)
*C07D 239/42* (2006.01)

(52) U.S. Cl.
CPC ............... *A01N 43/40* (2013.01); *A01N 43/82* (2013.01); *C07D 239/30* (2013.01); *A01N 43/80* (2013.01); *A01N 43/54* (2013.01); *C07D 413/12* (2013.01); *C07D 405/12* (2013.01); *C07D 413/06* (2013.01); *A01N 43/78* (2013.01); *C07D 417/12* (2013.01); *C07D 213/81* (2013.01); *A01N 43/72* (2013.01); *C07D 239/28* (2013.01); *C07D 239/47* (2013.01); *C07D 239/42* (2013.01)
USPC ........... 514/256; 514/336; 514/340; 514/342; 514/352

(58) Field of Classification Search
CPC ....... A01N 43/08; A01N 43/16; A01N 43/40; A01N 43/54; A01N 43/74; A01N 43/78; A01N 43/80; A01N 43/82; C07D 213/73; C07D 239/42; C07D 239/47; C07D 405/04; C07D 405/12; C07D 413/06; C07D 417/12
USPC .......... 514/256, 336, 340, 342, 352; 544/298, 544/329; 546/297, 309
See application file for complete search history.

(56) References Cited

U.S. PATENT DOCUMENTS

| 6,784,137 B2 | 8/2004 | Balko et al. |
| 7,300,907 B2 | 11/2007 | Epp et al. |
| 7,314,849 B2 | 1/2008 | Balko et al. |
| 2007/0197391 A1 | 8/2007 | Clark et al. |
| 2009/0062125 A1 | 3/2009 | Epp et al. |
| 2009/0088322 A1 | 4/2009 | Epp et al. |

FOREIGN PATENT DOCUMENTS

| EP | 1 498 413 | 1/2005 | |
| WO | WO 01/51468 | * 7/2001 | ........... C07D 213/79 |
| WO | WO 2004/035545 | 4/2004 | |
| WO | WO 2004/089906 | 10/2004 | |
| WO | WO2005/063721 | 7/2005 | |
| WO | WO2007/082076 | 7/2007 | |
| WO | WO 2007/082098 | 7/2007 | |
| WO | WO2010099279 | 2/2010 | |

OTHER PUBLICATIONS

Dorigo, et al., Synthesis and Cardiotonic Activity of Novel Pyrimidine Derivatives: Crystallographic and Quantum Chemical Studies, J. Med. Chem., 39, 3671-3683 (1996).*

* cited by examiner

*Primary Examiner* — Erich A Leeser
(74) *Attorney, Agent, or Firm* — Michael R. Asam

(57) ABSTRACT

N-Alkoxyamides of 4-aminopicolinic acids and 6-amino-4-pyrimidinecarboxylates are selective herbicides for corn, canola and sugar beet.

8 Claims, No Drawings

N-ALKOXYAMIDES OF 6-(SUBSTITUTED PHENYL)-4-AMINOPICOLINATES AND 2-(SUBSTITUTED PHENYL)-6-AMINO-4-PYRIMIDINE CARBOXYLATES AND THEIR USE AS SELECTIVE HERBICIDES FOR CROPS

RELATED APPLICATIONS

This application is a divisional of Ser. No. 12/12,483, filed 25, Feb. 2010; and claims the benefit of U.S. Provisional Application Ser. No. 61/156,088 filed on 27, Feb. 2009.

FIELD OF THE INVENTION

This invention relates to use of certain novel N-alkoxyamides of 6-(substituted phenyl)-4-aminopicolinates and 2-(substituted phenyl)-6-amino-4-pyrimidinecarboxylates as selective herbicides for corn, canola (oilseed rape) and sugar beet and to methods of making the compounds.

BACKGROUND OF THE INVENTION

A number of picolinic acids and their pesticidal properties have been described in the art. U.S. Pat. No. 6,784,137 B2 and U.S. Pat. No. 7,314,849 B2 disclose a genus of 6-aryl-4-aminopicolinic acids and their derivatives and their use as selective herbicides, particularly for rice and cereals such as wheat and barley. WO 2005/063721 A1, WO 2007/082076 A1, U.S. Patent Appl. Publ. 2009/0062125 A1, U.S. Patent Appl. Publ. 2009/0088322 A1, U.S. Patent Appl. Publ. 2007/0197391 A1 and U.S. Pat. No. 7,300,907 B2 disclose certain 2-substituted-6-amino-4-pyrimidinecarboxylic acids and their derivatives and their use as herbicides. It has now been discovered that crop selectivity of certain N-alkoxyamides of 6-(substituted phenyl)-4-aminopicolinates and of 2-(substituted phenyl)-6-amino-4-pyrimidinecarboxylates can be extended to corn, canola and sugar beet.

SUMMARY OF THE INVENTION

It has now been found that certain N-alkoxyamides of 6-(substituted phenyl)-4-aminopicolinates and of 2-(substituted phenyl)-6-amino-4-pyrimidinecarboxylates are superior herbicides with a broad spectrum of broadleaf weed control and with excellent selectivity to corn, canola and sugar beet. The compounds further possess excellent toxicological or environmental profiles.

The invention includes compounds of Formula I:

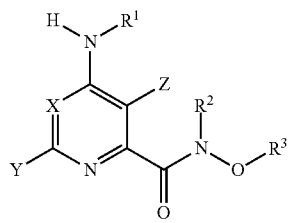

wherein
X represents CH, CF, or N;
Y represents halogen, $C_1$-$C_8$ alkyl, $C_3$-$C_6$ cycloalkyl, or phenyl substituted with 1-4 substituents independently selected from halogen, $C_1$-$C_3$ alkyl, $C_3$-$C_6$ cycloalkyl, $C_1$-$C_3$ alkoxy, $C_1$-$C_3$ haloalkyl, $C_1$-$C_3$ haloalkoxy, cyano, nitro, $N(R^4)_2$, or where two adjacent substituents are taken together as —OCH$_2$O—;
Z represents halogen, $C_1$-$C_3$ alkoxy, or $C_2$-$C_4$ alkenyl;
$R^1$ represents H, $C_1$-$C_3$ alkyl, $C_2$-$C_4$ acyl, or benzyl;
$R^2$ represents H, $C_1$-$C_3$ alkyl, or $C_2$-$C_4$ acyl;
$R^3$ represents H, $C_1$-$C_8$ alkyl, $C_3$-$C_8$ cycloalkyl, $C_1$-$C_8$ haloalkyl, $C_3$-$C_8$ alkoxyalkyl, $C_2$-$C_8$ cyanoalkyl, $C_2$-$C_8$ alkylcarbonyl, $C_2$-$C_8$ alkenyl, $C_5$-$C_8$ cycloalkenyl, $C_2$-$C_8$ haloalkenyl, $C_2$-$C_8$ alkynyl, unsubstituted or substituted phenyl, unsubstituted or substituted heteroaryl, unsubstituted or substituted heterocyclyl, alkylcycloalkyl, alkylcycloalkenyl, unsubstituted or substituted arylalkyl, or $R^2$ and $R^3$ together with the O and N atoms to which they are joined form an unsubstituted or substituted 5- to 7-membered ring optionally containing one further heteroatom selected from O, N, and S; and
$R^4$ represents H or $C_1$-$C_3$ alkyl.

Preferred compounds include those in which X represents CH or N, Y represents substituted phenyl, Z represents halogen or methoxy, $R^1$ and $R^2$ represent hydrogen, and $R^3$ represents $C_1$-$C_4$ alkyl, $C_2$-$C_6$ alkenyl or unsubstituted or para-substituted benzyl.

The invention includes herbicidal compositions comprising an herbicidally effective amount of a compound of Formula I in a mixture with an agriculturally acceptable adjuvant or carrier. The invention also includes a method of use of the compounds and compositions of the present invention to kill or control undesirable vegetation by application of an herbicidal amount of the compound to the vegetation or to the locus of the vegetation as well as to the soil prior to emergence of the vegetation. The invention further includes a method for the selective postemergent control of undesirable vegetation in the presence of corn, canola or sugar beet, which comprises applying to said undesirable vegetation an herbicidally effective amount of a compound of the present invention. The invention also includes a method of making the compounds of the present invention.

DETAILED DESCRIPTION OF THE INVENTION

The herbicidal compounds of the present invention are N-alkoxyamides of 6-(substituted phenyl)-4-aminopicolinic acids and 2-(substituted phenyl)-6-amino-4-pyrimidinecarboxylic acids and their derivatives. The picolinic acids from which the N-alkoxyamides of Formula I are derived are a new class of compounds having herbicidal activity. A number of picolinic acid compounds are described in U.S. Pat. No. 6,784,137 B2 and U.S. Pat. No. 7,314,849 B2, including 4-amino-3-chloro-6-(4-chloro-2-fluoro-3-methoxyphenyl)pyridine-2-carboxylic acid and 4-amino-3-chloro-6-(2,4-dichloro-3-methoxyphenyl)pyridine-2-carboxylic acid. The pyrimidinecarboxylic acids from which the N-alkoxyamides of Formula I are derived are also a new class of compounds having herbicidal activity. A number of pyrimidinecarboxylic acid compounds are described in WO 2005/063721 A1, WO 2007/082076 A1, U.S. Patent Appl. Publ. 2009/0062125 A1, U.S. Patent Appl. Publ. 2009/0088322 A1, U.S. Patent Appl. Publ. 2007/0197391 A1 and U.S. Pat. No. 7,300,907 B2. These picolinic acids and pyrimidinecarboxylic acids control annual grass weeds, broadleaf weeds, and sedges in rice and cereals, but are phytotoxic to corn, canola and sugar beet at commercially herbicidal doses.

Preferred N-alkoxyamide groups are those for which the concentration of herbicide that is required to reduce growth of broadleaf weeds by 80% ($GR_{80}$) is at least two times (2x) lower than the concentration of herbicide that causes damage to 20% of the crop (GR$_{20}$). Preferred N-alkoxyamide groups for corn include the N-methoxyamide, N-(2-methylpropoxy) amide, N-(2-propenyloxy)amide and N-(2-propynyloxy) amide. Preferred N-alkoxyamide groups for canola and sugar beet include the N-ethoxyamide.

An alkoxyamide can be prepared by reacting an acid chloride with a hydroxylamine or its conjugate acid, typically the hydrochloride salt, in the presence of a base. Representative bases include triethylamine, diisopropylethylamine, morpholine, and 1,8-diazabicyclo[5.4.0]undec-7-ene. Examples of appropriate solvents for such a reaction include dichloromethane, 1,2-dichloroethane, diethyl ether, tetrahydrofuran, and ethyl acetate. A typical reaction temperature range is from 0° C. to 75° C. and a typical reaction time ranges from 1 hour to 72 hours. The hydroxylamine or its conjugate acid can be prepared by reacting 2-hydroxyisoindoline-1,3-dione (N-hydroxyphthalimide) with an alkyl halide, such as in Kim et al., *Synth. Commun.* 1992, 22, 1427-1432, or with an alcohol, such as in Mitsunobu, *Synthesis* 1981, 1-28, followed by deprotection of the phthalimide group with hydrazine. O-((2R,3R,4S,5R,6R)-3,4,5-trimethoxy-6-(methoxymethyl) tetrahydro-2H-pyran-2-yl)hydroxylamine was prepared as in Crouse et al., PCT Int. Appl. WO 2009/102736 A1. O-(tert-Butyldimethylsilyl)-N-methylhydroxylamine was prepared as in Knight et al., *Tetrahedron* 1997, 53, 11411-11424. O-(Tetrahydrofuran-2-yl)hydroxylamine was prepared as in Ogawa et al., *J. Med. Chem.* 1998, 41, 5094-5107. An alkoxyamide can also be prepared by reacting an ester, typically the methyl ester or ethyl ester, with a hydroxylamine. Examples of appropriate solvents for such a reaction include tetrahydrofuran, 1,2-dimethoxyethane, N,N-dimethylformamide, dimethyl sulfoxide, methyl alcohol, ethyl alcohol and water. The typical reaction temperature range is from 23° C. to 100° C. and a typical reaction time range is from 1 hour to 120 hours. An alkoxyamide can also be prepared by reacting an acid with an hydroxylamine or its conjugate acid, typically the hydrochloride salt, in the presence of an activating agent and, optionally, a base. Representative activating agents include dicyclohexyl carbodiimide, 1-ethyl-3-(3-dimethylaminopropyl)carbodiimide hydrochloride, 1,1'-carbonyl diimidazole, N,N'-disuccinimidyl carbonate, benzotriazol-1-yl-oxy-tris-(dimethylamino)-phosphonium hexafluorophosphate, and 2-chloro-1-methylpyridinium iodide. Representative bases include triethylamine, diisopropylethylamine, 4-(dimethylamino)pyridine, morpholine, and 1,8-diazabicyclo[5.4.0]undec-7-ene. Examples of appropriate solvents for such a reaction include dichloromethane, 1,2-dichloroethane, diethyl ether, tetrahydrofuran, ethyl acetate, acetonitrile and N,N-dimethylformamide. The typical reaction temperature range is from 0° C. to 75° C. and a typical reaction time range is from 1 hour to 72 hours. There are two preferred embodiments, shown in Scheme 1. In the first, compound II is sequentially treated with 1-ethyl-3-(3-dimethylaminopropyl) carbodiimide hydrochloride, a hydroxylamine, and 4-(dimethylamino)pyridine in 1,2-dichloroethane at 23° C. for 18 hours to provide compound I. In the second, compound II is sequentially treated with 1,1'-carbonyldiimidazole and a hydroxylamine in N,N-dimethylformamide at ambient temperature for 4 hours to provide compound I.

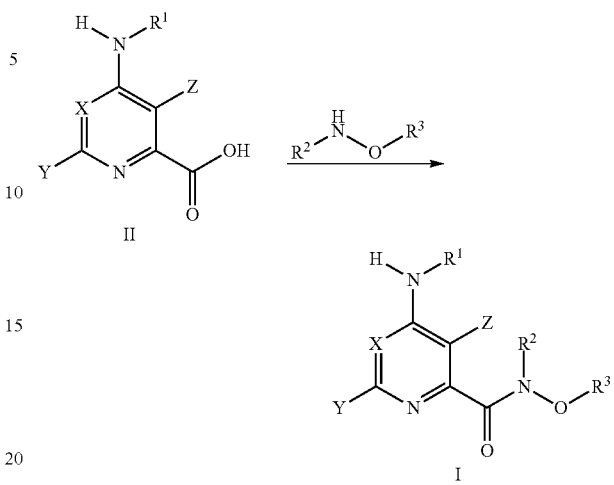

Scheme 1

It is recognized that some reagents and reaction conditions disclosed herein or in the chemical literature for preparing compounds of Formula I may not be compatible with certain functionalities present in the intermediates. In these instances, the incorporation of protection/deprotection sequences or functional group interconversions into the synthesis will aid in obtaining the desired products. The use and choice of the protecting groups will be apparent to one skilled in chemical synthesis.

One skilled in the art will recognize that, in some cases, after the introduction of a given reagent as disclosed herein or in the chemical literature, it may be necessary to perform additional routine synthetic steps not described in detail to complete the synthesis of compounds of Formula I. One skilled in the art will also recognize that it may be necessary to perform a combination of the steps disclosed herein or in the chemical literature in an order other than that implied by the particular sequence presented to prepare the compounds of Formula I.

Finally, one skilled in the art will also recognize that compounds of Formula I and the intermediates described herein or in the chemical literature can be subjected to various electrophilic, nucleophilic, radical, organometallic, oxidation, and reduction reactions to add substituents or modify existing substituents.

The terms "alkyl," "alkenyl" and "alkynyl," as well as derivative terms such as "alkoxy," "acyl," "alkylthio" and "alkylsulfonyl," as used herein, include within their scope straight chain, branched chain and cyclic moieties. Unless specifically stated otherwise, each may be unsubstituted or substituted with one or more substituents selected from but not limited to halogen, hydroxy, alkoxy, alkylthio, $C_1$-$C_6$ acyl, formyl, cyano, aryloxy or aryl, provided that the substituents are sterically compatible and the rules of chemical bonding and strain energy are satisfied. The terms "alkenyl" and "alkynyl" are intended to include one or more unsaturated bonds.

The term "aryl" refers to a phenyl or naphthyl group. The term "heteroaryl" refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more substituents selected from halogen, hydroxy, nitro, cyano, aryloxy, formyl, $C_1$-$C_6$ alkyl, $C_2$-$C_6$ alkenyl, $C_2$-$C_6$ alkynyl, $C_1$-$C_6$ alkoxy, halogenated $C_1$-$C_6$ alkyl, halogenated $C_1$-$C_6$ alkoxy, $C_1$-$C_6$ acyl, $C_1$-$C_6$ alkylthio, $C_1$-$C_6$ alkylsulfinyl, $C_1$-$C_6$ alkylsulfonyl, aryl, $C_1$-$C_6$ OC(O)alkyl, $C_1$-$C_6$ NHC(O)alkyl, C(O)OH, $C_1$-$C_6$C(O)Oalkyl, C(O)NH$_2$, $C_1$-$C_6$ C(O)NHalkyl, or $C_1$-$C_6$ C(O)N(alkyl)$_2$, provided that the substituents are sterically compatible and the rules of chemical bonding and strain energy are satisfied.

The term "heterocyclyl" refers to a 5- or 6-membered fully saturated or partially unsaturated ring containing one or more heteroatoms, viz., N, O or S; these heterocyclic rings may be fused to other non-aromatic systems.

The terms "tetrahydrofuranyl" and "tetrahydropyranyl" refer to 5- and 6-membered rings containing a single oxygen atom in addition to the 4 or 5 carbon atoms. The term "para-substituted benzyl" refers to a —CH$_2$C$_6$H$_5$ group in which the H in the 4-position is substituted with a substituent selected from the group consisting of halogen, $C_1$-$C_4$ alkyl or $C_1$-$C_4$ alkoxy.

Unless specifically limited otherwise, the term halogen includes fluorine, chlorine, bromine, and iodine.

The compounds of Formula I have been found to be useful as pre-emergence and post-emergence herbicides for corn, canola and sugar beet. The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinating seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote selective herbicidal action. Generally, it is preferred to apply the compounds of Formula I postemergence to relatively immature undesirable vegetation to achieve the maximum control of weeds.

Application rates of about 2 to about 140 grams per hectare (g/ha) are generally employed in postemergence operations; for preemergence applications, rates of about 4 to about 280 g/ha are generally employed.

The herbicidal compounds of the present invention are often applied in conjunction with one or more other herbicides to control a wider variety of undesirable vegetation. When used in conjunction with other herbicides, the presently claimed compounds can be formulated with the other herbicide or herbicides, tank mixed with the other herbicide or herbicides or applied sequentially with the other herbicide or herbicides. Some of the herbicides that can be employed in conjunction with the compounds of the present invention include: acetochlor, alachlor, asulam, atrazine, benazolin, benfuresate, bentazone, butachlor, butafenacil, butroxydim, carbetamide, clethodim, clomazone, clopyralid, cyanazine, cycloate, cycloxydim, 2,4-D, desmedipham, dicamba, diclofop-methyl, diflufenzopyr, dimefuron, dimethachlor, dimethenamid, dimethenamid-P, diquat, diuron, EPTC, ethofumesate, florasulam, fluazifop, fluazifop-P-butyl, flufenacet, flumetsulam, flumiclorac, flumicloracpentyl, fluroxypyr, foramsulfuron, fumiclorac, glufosinate, glufosinate-ammonium, glyphosate, halosulfuron, haloxyfop-methyl, haloxyfop-R-methyl, S-hydroxypyrazoles, isoxaflutole, KIH-845, lenacile, linuron, mesotrione, metazochlor, metolachlor, S-metolachlor, metosulam, metribuzin, napropamide, nicosulfuron, oxyfluorfen, pendimethalin, phenmedipham, picloram, primisulfuron, propachlor, propaquizafop, propyzamide (pronamide), prosulfuron, pyrazon, quinmerac, quizalofop-P-ethyl, quizalofop-P-tefuryl, rimsulfuron, sethoxydim, simazine, sulcotrione, sulfosate, tepraloxydim, terbuthylazin, thifensulfuron, thifensulfuron-methyl, triasulfuron-methyl, trifluralin and triflusulfuron-methyl. The herbicidal compounds of the present invention can, further, be used in conjunction with glyphosate, glufosinate, dicamba, imidazolinones or 2,4-D on glyphosate-tolerant, glufosinate-tolerant, dicamba-tolerant, imidazolinone-tolerant or 2,4-D-tolerant crops. It is generally preferred to use the compounds of the invention in combination with herbicides that are selective for the crop being treated and which complement the spectrum of weeds controlled by these compounds at the application rate employed. It is further generally preferred to apply the compounds of the invention and other complementary herbicides at the same time, either as a combination formulation or as a tank mix.

The compounds of the present invention can generally be employed in combination with known herbicide safeners, such as benoxacor, benthiocarb, brassinolide, cloquintocet (mexyl), cyometrinil, cyprosulfamate, daimuron, dichlormid, dicyclonon, dietholate, dimepiperate, disulfoton, fenchlorazole-ethyl, fenclorim, flurazole, fluxofenim, furilazole, isoxadifen-ethyl, mefenpyr-diethyl, mephenate, MG 191, MON 4660, naphthalic anhydride (NA), oxabetrinil, R29148 and N-phenyl-sulfonylbenzoic acid amides, to enhance their selectivity. They can additionally be employed to control undesirable vegetation in many crops that have been made tolerant to or resistant to them or to other herbicides by genetic manipulation or by mutation and selection. For example, corn, wheat, rice, soybean, sugar beet, cotton, canola, and other crops that have been made tolerant or resistant to compounds that are acetolactate synthase inhibitors in sensitive plants can be treated. Many glyphosate- and glufosinate-tolerant crops can be treated as well, alone or in combination with these herbicides. Some crops have been made tolerant to auxinic herbicides such as 2,4-(dichlorophenoxy) acetic acid (2,4-D) and dicamba. These herbicides may be used to treat such resistant crops or other auxin tolerant crops.

While it is possible to utilize the compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art. Some of these adjuvants include, but are not limited to, crop oil concentrate (mineral oil (85%)+emulsifiers (15%)); nonylphenol ethoxylate; benzylcocoalkyldimethyl quaternary ammonium salt; blend of petroleum hydrocarbon, alkyl esters, organic acid, and anionic surfactant; $C_9$-$C_{11}$ alkylpolyglycoside; phosphated alcohol ethoxylate; natural primary alcohol ($C_{12}$-$C_{16}$) ethoxylate; di-sec-butylphenol EO—PO block copolymer; polysiloxane-methyl cap; nonylphenol ethoxylate+urea ammonium nitrate; emulsified methylated seed oil; tridecyl alcohol (synthetic) ethoxylate (8EO); tallow amine ethoxylate (15 EO); PEG(400) dioleate-99.

Liquid carriers that can be employed include water and organic solvents. The organic solvents typically used include, but are not limited to, petroleum fractions or hydrocarbons such as mineral oil, aromatic solvents, paraffinic oils, and the like; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; esters of the above vegetable oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like. Specific organic solvents include toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methyl alcohol, ethyl alcohol, isopropyl alcohol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cottonseed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Surfactants conventionally used in the art of formulation and which may also be used in the present formulations are described, inter alia, in "McCutcheon's Detergents and Emulsifiers Annual," MC Publishing Corp., Ridgewood, N.J., 1998 and in "Encyclopedia of Surfactants," Vol. I-III, Chemical Publishing Co., New York, 1980-81. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutyl-naphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; salts of mono and dialkyl phosphate esters; vegetable oils such as soybean oil, rapeseed oil, olive oil, castor oil, sunflower seed oil, coconut oil, corn oil, cottonseed oil, linseed oil, palm oil, peanut oil, safflower oil, sesame oil, tung oil and the like; and esters of the above vegetable oils.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation water, and by other conventional means known to those skilled in the art.

The following Examples are presented to illustrate the various aspects of this invention and should not be construed as limitations to the claims.

EXAMPLES

Example 1

Preparation of O-(2-propynyl)hydroxylamine

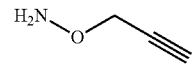

Hydrazine hydrate (530 microliters (μL), 11 millimoles (mmol), 1.1 equivalents (equiv)) was added to a stirred solution of 2-(2-propynyloxy)isoindoline-1,3-dione (2.0 grams (g), 10 mmol, 1.0 equiv) in dichloromethane ($CH_2Cl_2$; 50 milliliters (mL)) at 23° C. The resulting white suspension was stirred at 23° C. for 18 hours (h). The reaction mixture was vacuum filtered. The filtrate was diluted with a 0.1 molar (M) aqueous (aq) solution of sodium hydroxide (NaOH; 200 mL) and extracted with $CH_2Cl_2$ (3×50 mL). The combined organic layers were dried over sodium sulfate ($Na_2SO_4$), gravity filtered, and concentrated by rotary evaporation to afford a colorless oil (500 milligrams (mg), 46%): $^1$H NMR (300 MHz, $CDCl_3$) δ 5.60 (br s, 2H), 4.30 (d, J=2 Hz, 2H), 2.46 (t, J=2 Hz, 1H).

Other compounds prepared by the method of Example 1 above include:

O-((2-Chlorothiazol-5-yl)methyl)hydroxylamine

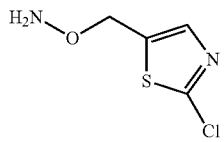

The title compound (540 mg, 96%) was isolated as a yellow powder: $^1$H NMR (300 MHz, CDCl$_3$) δ 7.47 (s, 1H), 5.52 (br s, 2H), 4.75 (s, 2H).

Example 2

Preparation of tert-butyl 2-propenyloxycarbamate

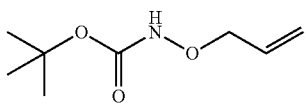

Di-tert-butyl dicarbonate (11 g, 50 mmol, 1.1 equiv) and powdered NaOH (3.7 g, 91 mmol, 2.0 equiv) were sequentially added to a stirred biphasic mixture of O-2-propenylhydroxyl-amine hydrochloride (5.0 g, 46 mmol, 1.0 equiv) in 1:1 CH$_2$Cl$_2$:water (150 mL) at 23° C. The resulting white biphasic mixture was vigorously stirred at 23° C. for 18 h. The reaction mixture was diluted with water (H$_2$O; 100 mL) and extracted with CH$_2$Cl$_2$ (100 mL). The organic layer was dried over Na$_2$SO$_4$, gravity filtered, and concentrated by rotary evaporation to afford a colorless oil (7.3 g, 92%): $^1$H NMR (300 MHz, CDCl$_3$) δ 7.11 (br s, 1H), 5.96 (m, 1H), 5.31 (m, 2H), 4.34 (dt, J=6, 1 Hz, 2H), 1.48 (s, 9H).

Example 3

Preparation of tert-butyl 2-propenyloxy(methyl)carbamate

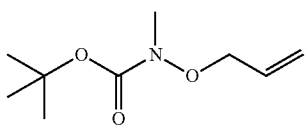

Sodium hydride (NaH, 60% dispersion in mineral oil; 390 mg, 9.7 mmol, 1.1 equiv) was added to a stirred solution of tert-butyl 2-propenyloxycarbamate (2.0 g, 8.8 mmol, 1.0 equiv) in tetrahydrofuran (THF; 23 mL) at 0° C. The resulting bubbling white mixture was warmed to 23° C. and stirred for 15 minutes (min). Iodomethane (660 µL, 11 mmol, 1.2 equiv) was added and the resulting colorless solution was stirred at 23° C. for 18 h. The reaction mixture was diluted with H$_2$O (100 mL) and extracted with CH$_2$Cl$_2$ (3×75 mL). The combined organic layers were dried over magnesium sulfate (MgSO$_4$), gravity filtered, and concentrated by rotary evaporation to afford a yellow oil (1.6 g, 99%): $^1$H NMR (300 MHz, CDCl$_3$) δ 5.98 (m, 1H), 5.37-5.24 (m, 2H), 4.33 (dt, J=6, 1 Hz, 2H), 3.10 (s, 3H), 1.49 (s, 9H).

Example 4

Preparation of O-2-propenyl-N-methylhydroxylamine

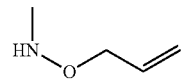

Triethylsilane (1.5 mL, 9.4 mmol, 1.1 equiv) and trifluoroacetic acid (6.3 mL, 85 mmol, 10 equiv) were sequentially added to a stirred solution of tert-butyl 2-propenyloxy(methyl)-carbamate (1.6 g, 8.5 mmol, 1.0 equiv) in CH$_2$Cl$_2$ (21 mL) at 0° C. The resulting pale pink solution was warmed to 23° C. and stirred for 20 h. The reaction mixture was carefully diluted with a saturated (satd) aq solution of sodium bicarbonate (NaHCO$_3$; 200 mL) and extracted with CH$_2$Cl$_2$ (3×70 mL). The combined organic layers were dried over MgSO$_4$, gravity filtered, and concentrated by rotary evaporation to afford a pale yellow oil (370 mg, 50%): $^1$H NMR (300 MHz, CDCl$_3$) δ 5.95 (m, 1H), 5.32-5.17 (m, 2H), 4.20 (dt, J=6, 1 Hz, 2H), 2.74 (s, 3H).

Example 5

Preparation of O-(2-methyl-2-propenyl)hydroxylamine

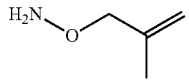

3-Bromo-2-methylpropene (1.4 mL, 13 mmol, 1.1 equiv) and 1,8-diazabicyclo[5.4.0]undec-7-ene (DBU; 1.8 mL, 12 mmol, 1.0 equiv) were sequentially added to a stirred solution of 2-hydroxyisoindoline-1,3-dione (N-hydroxyphthalimide; 2.0 g, 12 mmol, 1.0 equiv) in N,N-dimethylformamide (DMF; 30 mL) at 23° C. The resulting solution, which turned from yellow to dark red to colorless over ~5 min, was stirred at 23° C. for 18 h. The reaction mixture was diluted with 1 M aq hydrochloric acid (HCl; 300 mL). The resulting white precipitate was vacuum filtered and rinsed with H$_2$O to afford a white powder (2.3 g), which was dissolved in CH$_2$Cl$_2$ (53 mL). Hydrazine hydrate (570 µL, 12 mmol, 1.1 equiv) was added and the resulting white suspension was stirred at 23° C. for 18 h. The reaction mixture was vacuum filtered. The filtrate was diluted with 0.1 M aq NaOH (200 mL) and extracted with CH$_2$Cl$_2$ (3×50 mL). The combined organic layers were dried over Na$_2$SO$_4$, gravity filtered, and concentrated by rotary evaporation to afford a white semisolid (590 mg, 64%):

$^1$H NMR (300 MHz, CDCl$_3$) δ 5.34 (br s, 2H), 4.97 (m, 2H), 4.09 (s, 2H), 1.76 (br s, 3H).

Other compounds prepared by the method of Example 5 above include:

O-(2-Chloro-2-propenyl)hydroxylamine

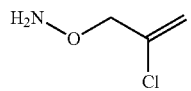

The title compound (800 mg, 73%) was isolated as a pale yellow oil: $^1$H NMR (300 MHz, CDCl$_3$) δ 5.56 (br s, 2H), 5.46 (q, J=1 Hz, 1H), 5.43 (m, 1H), 4.23 (s, 2H).

(E)-O-(2-Butenyl)hydroxylamine

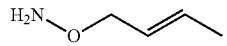

The title compound (340 mg, 61%) was isolated as a pale yellow oil: $^1$H NMR (300 MHz, CDCl$_3$) δ 5.78 (m, 1H), 5.60 (m, 1H), 4.91 (br s, 2H), 4.09 (dt, J=6, 1 Hz, 2H), 1.74 (m, 3H).

(E)-O-(3-Chloro-2-propenyl)hydroxylamine

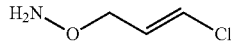

The title compound (340 mg, 61%) was isolated as a pale yellow oil: $^1$H NMR (300 MHz, CDCl$_3$) δ 6.28 (m, 1H), 6.11-6.01 (m, 1H), 5.42 (br s, 2H), 4.14 (m, 2H).

O-(2-Cyclohexenyl)hydroxylamine

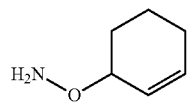

The title compound (910 mg, 76%) was isolated as a pale orange oil: $^1$H NMR (300 MHz, CDCl$_3$) δ 5.92 (m, 1H), 5.79 (m, 1H), 4.07 (m, 1H), 2.10-1.51 (m, 6H).

O-(Cyclopropylmethyl)hydroxylamine

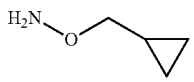

The title compound (520 mg, 65%) was isolated as a pale yellow oil: $^1$H NMR (300 MHz, CDCl$_3$) δ 5.41 (br s, 2H), 3.49 (d, J=7 Hz, 2H), 1.06 (m, 1H), 0.53 (m, 2H), 0.23 (m, 2H).

O-(But-3-en-2-yl)hydroxylamine

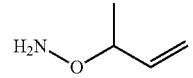

The title compound (530 mg, 63%) was isolated as a pale yellow oil: $^1$H NMR (300 MHz, CDCl$_3$) δ 5.79 (ddd, J=17, 10, 7 Hz, 1H), 5.29-5.16 (m, 4H), 4.05 (m, 1H), 1.23 (d, J=7 Hz, 3H).

O-(2-Fluoro-2-propenyl)hydroxylamine

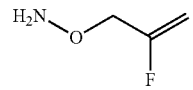

The title compound (410 mg, 45%) was isolated as a pale yellow oil: $^1$H NMR (300 MHz, CDCl$_3$) δ 5.57 (br s, 2H), 4.79 (dd, J=16, 3 Hz, 1H), 4.58 (dd, J=49, 3 Hz, 1H), 4.18 (d, J=15 Hz, 2H).

O-(3-Butenyl)hydroxylamine

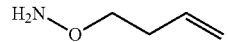

The title compound (320 mg, 50%) was isolated as a pale yellow oil: $^1$H NMR (300 MHz, CDCl$_3$) δ 5.81 (m, 1H), 5.38 (br s, 2H), 5.15-5.02 (m, 2H), 3.72 (t, J=7 Hz, 2H), 2.35 (m, 2H).

(E)-O-(2-Pentenyl)hydroxylamine

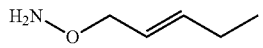

The title compound (480 mg, 99%) was isolated as a pale yellow oil: $^1$H NMR (300 MHz, CDCl$_3$) δ 5.81 (m, 1H), 5.56 (m, 1H), 5.31 (br s, 2H), 4.12 (dq, J=7, 1 Hz, 2H), 2.09 (m, 2H), 1.01 (t, J=8 Hz, 3H).

O-Butylhydroxylamine

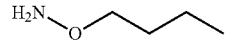

The title compound (880 mg, 94%) was isolated as a colorless oil: $^1$H NMR (300 MHz, CDCl$_3$) δ 5.34 (br s, 2H), 3.66 (t, J=7 Hz, 2H), 1.54 (m, 2H), 1.36 (m, 2H), 0.92 (t, J=7 Hz, 3H).

O-((2-Methoxyethoxy)methyl)hydroxylamine

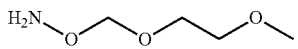

The title compound (320 mg, 55%) was isolated as a colorless oil: $^1$H NMR (300 MHz, CDCl$_3$) δ 5.57 (br s, 2H), 4.80 (s, 2H), 3.75 (m, 2H), 3.58 (m, 2H), 3.40 (s, 3H).

Example 6

Preparation of O-(furan-3-ylmethyl)hydroxylamine

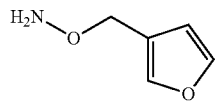

Furan-3-ylmethanol (1.1 mL, 12 mmol, 1.0 equiv) was added to a stirred suspension of 2-hydroxyisoindoline-1,3-dione (N-hydroxyphthalimide; 2.0 g, 12 mmol, 1.0 equiv) and triphenylphosphine (3.2 g, 12 mmol, 1.0 equiv) in THF (40 mL). The reaction vessel was equipped with an addition funnel containing diisopropyl azodicarboxylate (DIAD; 2.4 mL, 12 mmol, 1.0 equiv) and THF (21 mL) and that solution was added dropwise over 30 min. The resulting orange solution was stirred at 23° C. for 20 h. The reaction mixture was diluted with H$_2$O (150 mL) and extracted with diethyl ether (Et$_2$O; 3×70 mL). The combined organic layers were dried (MgSO$_4$), gravity filtered, and concentrated by rotary evaporation. The residue was purified by silica gel column chromatography (33% ethyl acetate (EtOAc) in hexane) to afford a white powder (620 mg), which was dissolved in CH$_2$Cl$_2$ (10 mL).

Hydrazine hydrate (190 μL, 3.8 mmol, 1.5 equiv) was added and the resulting white suspension was stirred at 23° C. for 24 h. The reaction mixture was vacuum filtered. The filtrate was diluted with 0.1 M aq NaOH (150 mL) and was extracted with CH$_2$Cl$_2$ (3×40 mL). The combined organic layers were dried over Na$_2$SO$_4$, gravity filtered, and concentrated by rotary evaporation to afford a colorless oil (250 mg, 86%): $^1$H NMR (300 MHz, CDCl$_3$) δ 7.46 (m, 1H), 7.41 (t, J=2 Hz, 1H), 6.45 (m, 1H), 5.39 (br s, 2H), 4.56 (s, 2H).

Other compounds prepared by the method of Example 6 above include:

O-(Thiazol-5-ylmethyl)hydroxylamine

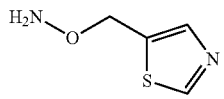

The title compound (320 mg, 73%) was isolated as a pale yellow oil: $^1$H NMR (300 MHz, CDCl$_3$) δ 8.80 (s, 1H), 7.84 (s, 1H), 5.52 (br s, 2H), 4.89 (s, 2H).

O-(Furan-2-ylmethyl)hydroxylamine

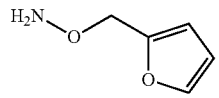

The title compound (250 mg, 50%) was isolated as a pale yellow oil: $^1$H NMR (300 MHz, CDCl$_3$) δ 7.43 (dd, J=2, 1 Hz, 1H), 6.43-6.35 (m, 2H), 5.46 (br s, 2H), 4.63 (s, 2H).

Example 7

Preparation of Isoxazolidine Hydrochloride

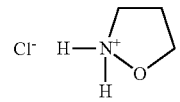

1,3-Dichloropropane (1.6 mL, 15 mmol, 1.2 equiv) and DBU (1.8 mL, 12 mmol, 1.0 equiv) were sequentially added to a stirred solution of 2-hydroxyisoindoline-1,3-dione (N-hydroxyphthalimide; 2.0 g, 12 mmol, 1.0 equiv) in DMF (30 mL) at 23° C. The resulting dark red solution was heated to 50° C. and stirred for 18 h. The resulting colorless solution was diluted with 1 M aq HCl (300 mL) and extracted with Et$_2$O (2×100 mL). The combined organic layers were dried (MgSO$_4$), gravity filtered, and concentrated by rotary evaporation to afford a colorless oil (1.5 g), which was dissolved in ethanol (EtOH; 15 mL). Hydrazine hydrate (300 μL, 11 mmol, 1.0 equiv) was added and the resulting pale yellow suspension was stirred at 23° C. for 4 h. The reaction mixture was vacuum filtered and the filtrate was concentrated by rotary evaporation to afford a pale yellow powder (530 mg, 77%): $^1$H NMR (300 MHz, DMSO-d$_6$) δ 5.34 (br s, 2H), 4.07 (t, J=7 Hz, 2H), 3.37 (t, J=7 Hz, 2H), 2.30 (p, J=7 Hz, 2H).

Example 8

Preparation of O-(cyclohexenylmethyl)hydroxylamine

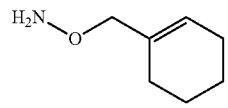

Methylenecyclohexane (5.0 g, 52 mmol, 10 equiv) was added to a stirred suspension of 2-hydroxyisoindoline-1,3-dione (N-hydroxyphthalimide; 850 mg, 5.2 mmol, 1.0 equiv), iodobenzenediacetate (1.7 g, 5.2 mmol, 1.0 equiv), and copper(I) chloride (52 mg, 0.52 mmol, 0.10 equiv) in acetonitrile (17 mL) at 23° C. The resulting vibrant blue/green mixture was heated to 70° C. and stirred for 12 h. The cooled reaction mixture was diluted with 1 M aq HCl (150 mL) and extracted with CH$_2$Cl$_2$ (1×75 mL). The organic layer was dried (MgSO$_4$), gravity filtered, and concentrated by rotary evaporation. The residue was purified by silica gel column chromatography (25% EtOAc in hexane) to afford a colorless semi-solid (400 mg), which was dissolved in CH$_2$Cl$_2$ (8 mL). Hydrazine hydrate (90 μL, 1.9 mmol, 1.2 equiv) was added and the resulting white suspension was stirred at 23° C. for 24 h. The reaction mixture was vacuum filtered. The filtrate was diluted with 0.1 M aq NaOH (50 mL) and extracted with CH$_2$Cl$_2$ (3×40 mL). The combined organic layers were dried over Na$_2$SO$_4$, gravity filtered, and concentrated by rotary evaporation to afford a mixture of isomers as a colorless oil (180 mg, 90%): $^1$H NMR (300 MHz, CDCl$_3$) δ 5.74 (br s, 1H), 5.24 (br s, 2H), 4.03 (s, 2H), 2.10-1.97 (m, 4H), 1.69-1.56 (m, 4H).

Example 9

Preparation of 4-amino-3-chloro-6-(4-chloro-2-fluoro-3-methoxyphenyl)-N-(2-methylpropoxy)picolinamide (Compound 1)

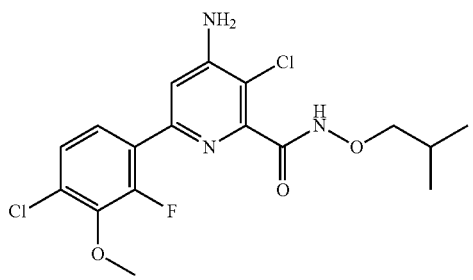 [SMILES: COc1c(Cl)ccc(-c2cc(N)c(Cl)c(C(=O)NOCC(C)C)n2)c1F]

O-iso-Butylhydroxylamine hydrochloride (380 mg, 3.0 mmol, 2.0 equiv) and 4-(dimethylamino)pyridine (740 mg, 6.0 mmol, 4.0 equiv) were sequentially added to a stirred suspension of 4-amino-3-chloro-6-(4-chloro-2-fluoro-3-methoxyphenyl)picolinic acid (prepared as in Balko et al., U.S. Pat. No. 7,314,849 B2; 500 mg, 1.5 mmol, 1.0 equiv) and 1-ethyl-3-(3-dimethylaminopropyl)-carbodiimide hydrochloride (1.2 g, 6.0 mmol, 4.0 equiv) in 1,2-dichloroethane (5.0 mL) at 23° C. The resulting tan suspension was stirred at 23° C. for 18 h. The reaction mixture was quenched with glacial acetic acid (430 μL, 7.5 mmol, 5.0 equiv) and concentrated by a nitrogen stream. The residue was directly subjected to silica gel column chromatography (50% EtOAc in hexane) to afford a white powder (370 mg, 61%): mp 145-148° C.; $^1$H NMR (300 MHz, CDCl$_3$) δ 9.87 (br s, 1H), 7.53 (t, J=8 Hz, 1H), 7.26 (m, 1H), 7.18 (d, J=2 Hz, 1H), 4.95 (br s, 2H), 3.99 (d, J=1 Hz, 3H), 3.83 (d, J=7 Hz, 2H), 2.07 (m, 1H), 1.01 (d, J=6 Hz, 6H); IR (neat film) 3221 (m), 2941 (w), 2878 (w), 1653 (s) cm$^{-1}$; ESIMS m/z 402.2 ([M+H]$^+$).

Other compounds prepared from known or previously described starting materials by the method of Example 9 above include:

4-Amino-3-chloro-6-(4-chloro-2-fluoro-3-methoxyphenyl)-N-methoxypicolinamide (Compound 2)

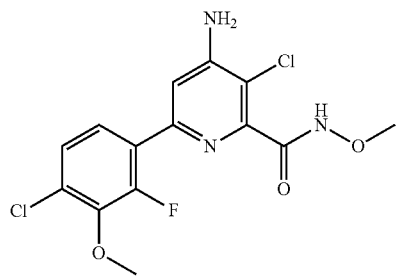 [SMILES: CONC(=O)c1nc(-c2ccc(Cl)c(OC)c2F)cc(N)c1Cl]

The title compound (270 mg, 50%) was isolated as a white powder: mp 215-217° C.; $^1$H NMR (300 MHz, CDCl$_3$) δ 9.94 (br s, 1H), 7.54 (dd, J=8, 9 Hz, 1H), 7.26 (dd, J=2, 9 Hz, 1H), 7.19 (d, J=2 Hz, 1H), 4.95 (br s, 2H), 3.99 (d, J=1 Hz, 3H), 3.91 (s, 3H); IR (neat film) 3455 (m), 3333 (m), 3284 (m), 3230 (w), 2948 (w), 1680 (s), 1626 (m) cm$^{-1}$; ESIMS m/z 360.1 ([M+H]$^+$).

N-(2-Propenyloxy)-4-amino-3-chloro-6-(4-chloro-2-fluoro-3-methoxyphenyl)picolinamide (Compound 3)

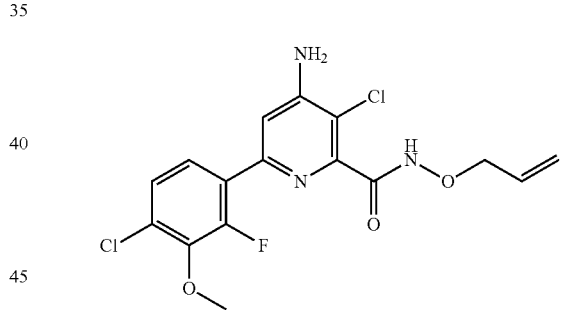

The title compound (230 mg, 62%) was isolated as a white powder: mp 169-172° C.; $^1$H NMR (300 MHz, CDCl$_3$) δ 9.87 (br s, 1H), 7.53 (dd, J=1, 7 Hz, 1H), 7.25 (dd, J=1, 7 Hz, 1H), 7.20 (d, J=2 Hz, 1H), 6.07 (m, 1H), 5.45-5.32 (m, 2H), 4.95 (br s, 2H), 4.54 (d, J=7 Hz, 2H), 3.99 (d, J=1 Hz, 3H); IR (neat film) 3484 (m), 3291 (m), 3196 (m), 2946 (w), 1679 (s), 1629 (s) cm$^{-1}$; ESIMS m/z 386.2 ([M+H]$^+$).

Compound 3 was also prepared in the following manner. 4-Amino-3-chloro-6-(4-chloro-2-fluoro-3-methoxyphenyl)picolinic acid (29.6 g, 89.39 mmol) was dissolved in anhydrous DMF (280 mL) under nitrogen. 1,1'-Carbonyldiimidazole (16.16 g, 99.66 mmol, 1.1 equiv) was added. After stiffing for 30 min, solid O-allylhydroxylamine hydrochloride (11.11 g, 101.41 mmol, 1.1 equiv) was added. After 3 h, the reaction mixture was poured into H$_2$O (1400 mL). The resulting precipitate was filtered, washed with H$_2$O and dried to give a white solid (32.1 g, 93%) which was found to be 98% pure by high-performance liquid chromatography (HPLC). $^1$H NMR and LC-MS data matched that above.

4-Amino-3-chloro-6-(4-chloro-2-fluoro-3-methoxyphenyl)-N-ethoxypicolinamide (Compound 4)

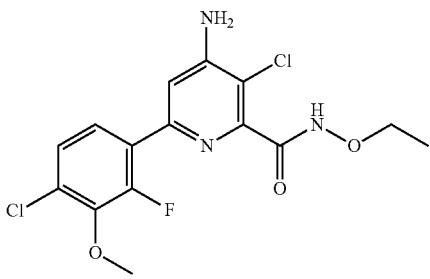 [SMILES: CCONC(=O)c1nc(-c2ccc(Cl)c(OC)c2F)cc(N)c1Cl]

The title compound (150 mg, 26%) was isolated as a white powder: mp 192-195° C.; ¹H NMR (300 MHz, CDCl₃) δ 9.85 (br s, 1H), 7.53 (t, J=8 Hz, 1H), 7.26 (m, 1H), 7.18 (d, J=2 Hz, 1H), 4.94 (s, 2H), 4.12 (q, J=7 Hz, 2H), 3.99 (s, 3H), 1.35 (t, J=7 Hz, 3H); IR (neat film) 3487 (m), 3301 (m), 3198 (m), 2973 (w), 2943 (w), 1684 (s), 1627 (s) cm⁻¹; ESIMS m/z 374.2 ([M+H]⁺).

4-Amino-N-(benzyloxy)-3-chloro-6-(4-chloro-2-fluoro-3-methoxyphenyl)picolinamide (Compound 5)

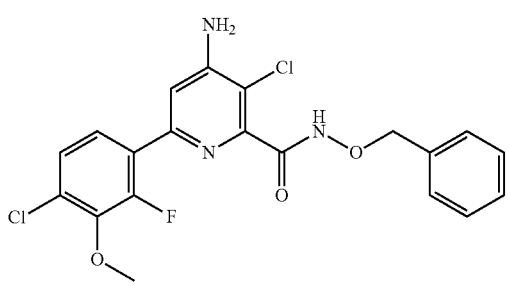 [SMILES: COc1c(Cl)ccc(-c2cc(N)c(Cl)c(C(=O)NOCc3ccccc3)n2)c1F]

The title compound (110 mg, 17%) was isolated as an off-white powder: mp 166-169° C.; ¹H NMR (300 MHz, CDCl₃) δ 9.77 (br s, 1H), 7.53-7.34 (m, 5H), 7.27-7.16 (m, 3H), 5.10 (s, 2H), 4.95 (br s, 2H), 4.00 (s, 3H); IR (neat film) 3483 (m), 3358 (m), 3200 (m), 2939 (w), 1654 (s), 1621 (s) cm⁻¹; ESIMS m/z 434.0 ([M−H]⁻).

4-Amino-3-chloro-6-(4-chloro-2-fluoro-3-methoxyphenyl)-N-methoxy-N-methyl-picolinamide (Compound 6)

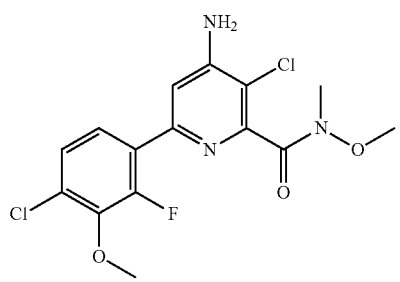 [SMILES: COc1c(Cl)ccc(-c2cc(N)c(Cl)c(C(=O)N(C)OC)n2)c1F]

The title compound (450 mg, 79%) was isolated as a white powder: mp 159-162° C.; ¹H NMR (300 MHz, CDCl₃) δ 7.66 (t, J=8 Hz, 1H), 7.21 (dd, J=1, 8 Hz, 1H), 7.13 (d, J=1 Hz, 1H), 4.75 (br s, 2H), 3.97 (s, 3H), 3.62 (s, 3H), 3.41 (s, 3H); IR (neat film) 3437 (m), 3343 (m), 3243 (m), 2984 (w), 2941 (w), 1648 (s) cm⁻¹; ESIMS m/z 371.9 ([M−H]⁻).

4-Amino-3-chloro-6-(4-chloro-2-fluoro-3-methoxyphenyl)-N-propoxypicolinamide (Compound 7)

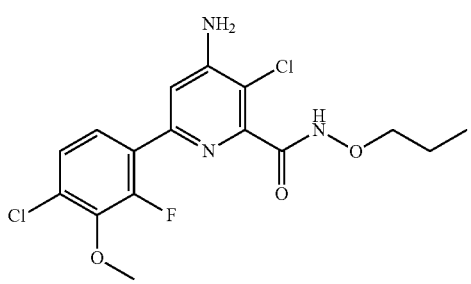 [SMILES: CCCONC(=O)c1nc(-c2ccc(Cl)c(OC)c2F)cc(N)c1Cl]

The title compound (250 mg, 42%) was isolated as an off-white powder: mp 165-168° C.; ¹H NMR (300 MHz, CDCl₃) δ 9.86 (br s, 1H), 7.54 (t, J=8 Hz, 1H), 7.26 (m, 1H), 7.19 (d, J=2 Hz, 1H), 4.95 (s, 2H), 4.05-3.96 (m, 5H), 1.76 (m, 2H), 1.02 (t, J=7 Hz, 3H); IR (neat film) 3485 (m), 3349 (m), 3209 (m), 2967 (m), 2941 (m), 2879 (w), 1653 (s), 1629 (s) cm⁻¹; ESIMS m/z 388.2 ([M+H]⁺).

4-Amino-3-chloro-6-(4-chloro-2-fluoro-3-methoxyphenyl)-N-isopropoxypicolinamide (Compound 8)

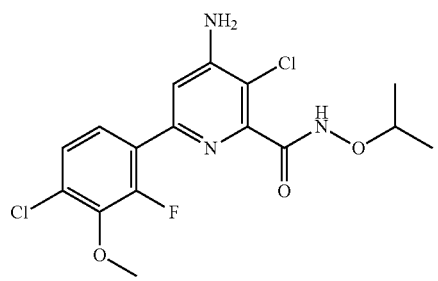 [SMILES: COc1c(Cl)ccc(-c2cc(N)c(Cl)c(C(=O)NOC(C)C)n2)c1F]

The title compound (360 mg, 61%) was isolated as a white powder: mp 190-193° C.; ¹H NMR (300 MHz, CDCl₃) δ 9.74 (br s, 1H), 7.56 (t, J=8 Hz, 1H), 7.26 (m, 1H), 7.21 (d, J=2 Hz, 1H), 4.97 (br s, 2H), 4.33 (h, J=6 Hz, 1H), 4.01 (s, 3H), 1.35

(d, J=6 Hz, 6H); IR (neat film) 3483 (w), 3338 (m), 3213 (m), 2975 (w), 2936 (w), 1653 (s), 1621 (s) cm$^{-1}$; ESIMS m/z 388.2 ([M+H]$^+$).

N-Acetyl-N-(2-propenyloxy)-6-amino-2-(4-chloro-2-fluoro-3-methoxyphenyl)-5-vinylpyrimidine-4-carboxamide (Compound 9)

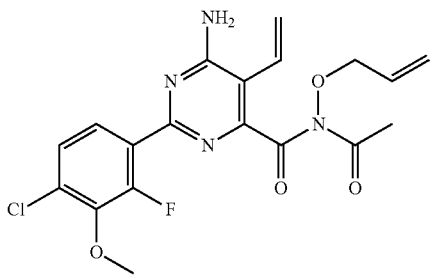 [SMILES: C=CCON(C(C)=O)C(=O)c1nc(-c2ccc(Cl)c(OC)c2F)nc(N)c1C=C]

The title compound (120 mg, 50%) was isolated as a white foam: $^1$H NMR (300 MHz, CDCl$_3$) δ 7.61 (dd, J=7, 8 Hz, 1H), 7.21 (dd, J=2, 8 Hz, 1H), 6.52 (dd, J=12, 18 Hz, 1H), 5.81 (m, 1H), 5.73-5.62 (m, 2H), 5.37 (br s, 2H), 5.29-5.21 (m, 2H), 4.60 (d, J=7 Hz, 2H), 3.99 (d, J=1 Hz, 3H), 2.50 (s, 3H); IR (neat film) 3462 (m), 3364 (s), 3212 (m), 3091 (w), 3008 (w), 2943 (w), 1730 (s), 1632 (m) cm$^-$; ESIMS m/z 421.3 ([M+H]$^+$).

N-(2-Propenyloxy)-6-amino-2-(4-chloro-2-fluoro-3-methoxyphenyl)-5-vinylpyrimidine-4-carboxamide (Compound 10)

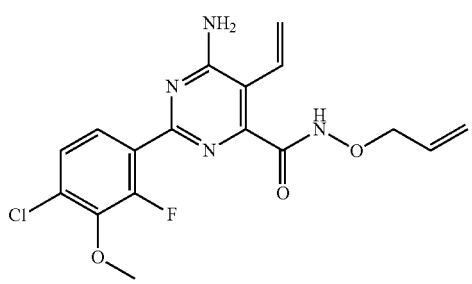 [SMILES: C=CCONC(=O)c1nc(-c2ccc(Cl)c(OC)c2F)nc(N)c1C=C]

The title compound (120 mg, 50%) was isolated as a pale yellow powder: mp 98-101° C.; $^1$H NMR (300 MHz, CDCl$_3$) δ 10.30 (br s, 1H), 7.69 (dd, J=7, 8 Hz, 1H), 7.31 (m, 1H), 7.24 (dd, J=2, 8 Hz, 1H), 6.06 (m, 1H), 5.74-5.54 (m, 4H), 5.45-5.32 (m, 2H), 4.51 (d, J=7 Hz, 2H), 4.01 (d, J=1 Hz, 3H); IR (neat film) 3465 (w), 3348 (m), 3198 (m), 3081 (w), 3005 (w), 2941 (w), 1663 (s), 1638 (m) cm$^{-1}$; ESIMS m/z 379.2 ([M+H]$^+$).

N-(2-Propenyloxy)-6-amino-5-chloro-2-cyclopropylpyrimidine-4-carboxamide (Compound 11)

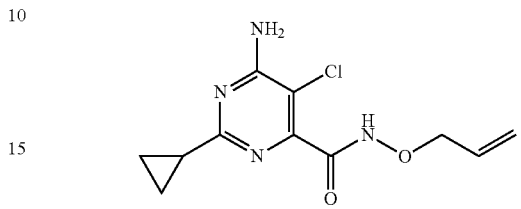

The title compound (75 mg, 24%) was isolated as a tan foam: $^1$H NMR (300 MHz, CDCl$_3$) δ 9.94 (br s, 1H), 6.05 (m, 1H), 5.50 (br s, 2H), 5.44-5.29 (m, 2H), 4.51 (d, J=6 Hz, 2H), 1.98 (m, 1H), 1.07-0.94 (m, 4H); IR (neat film) 3314 (m), 3177 (m), 3010 (w), 2931 (w), 1684 (s), 1641 (m) cm$^{-1}$; ESIMS m/z 269.2 ([M+H]$^+$).

Example 10

Preparation of 4-amino-3-chloro-6-(4-chloro-2-fluoro-3-methoxyphenyl)-N-(tetrahydro-2H-pyran-2-yloxy)picolinamide (Compound 12)

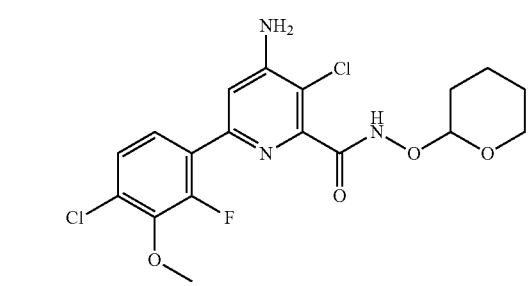 [SMILES: COc1c(Cl)ccc(-c2cc(N)c(Cl)c(C(=O)NOC3CCCCO3)n2)c1F]

1,1'-Carbonyl diimidazole (110 mg, 0.66 mmol, 1.1 equiv) was added to a stirred suspension of 4-amino-3-chloro-6-(4-chloro-2-fluoro-3-methoxyphenyl)picolinic acid (200 mg, 0.60 mmol, 1.0 equiv) in THF (3.0 mL) at 23° C. The resulting off-white suspension was stirred at 23° C. for 30 min. O-(Tetrahydro-2H-pyran-2-yl)hydroxylamine (85 mg, 0.72 mmol, 1.2 equiv) was added and the off-white suspension was stirred at 23° C. for 18 h. The reaction mixture was concentrated by a nitrogen stream, and the residue was directly subjected to silica gel column chromatography (5% methanol in chloroform) to afford a white powder (180 mg, 69%): mp 176-179° C.; $^1$H NMR (300 MHz, DMSO-d$_6$) δ 7.66 (t, J=8 Hz, 1H), 7.42 (dd, J=2, 8 Hz, 1H), 7.20 (d, J=2 Hz, 1H), 6.75 (br s, 2H), 5.01 (m, 1H), 4.05-3.90 (m, 4H), 3.50 (m, 1H), 1.77-1.66 (m, 3H), 1.60-1.47 (m, 3H); IR (neat film) 3325 (w), 3198 (w), 2946 (m), 2873 (w), 1682 (s), 1634 (s) cm$^{-1}$; ESIMS m/z 430.3 ([M+H]$^+$).

Other compounds prepared from known or previously described starting materials by the method of Example 10 above include:

4-Amino-3-chloro-6-(4-chloro-2-fluoro-3-methoxyphenyl)-N-(2-propynyloxy)picolinamide (Compound 13)

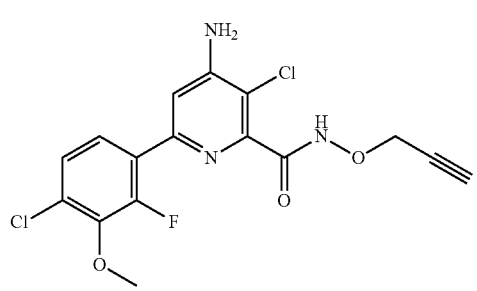 [SMILES: C#CCONC(=O)c1nc(-c2ccc(Cl)c(OC)c2F)cc(N)c1Cl]

The title compound (170 mg, 49%) was isolated as a white powder: mp 180-183° C.; $^1$H NMR (300 MHz, DMSO-d$_6$) δ 7.70 (t, J=8 Hz, 1H), 7.42 (dd, J=2, 8 Hz, 1H), 7.22 (d, J=2 Hz, 1H), 6.79 (br s, 2H), 4.58 (d, J=2 Hz, 2H), 3.93 (s, 3H), 3.63 (t, J=2 Hz, 1H); IR (neat film) 3453 (m), 3361 (m), 3291 (m), 2947 (w), 2120 (w), 1701 (s), 1639 (s) cm$^{-1}$; ESIMS m/z 384.2 ([M+H]$^+$).

4-Amino-3-chloro-6-(4-chloro-2-fluoro-3-methoxyphenyl)-N-(4-methyl-benzyloxy)picolinamide (Compound 14)

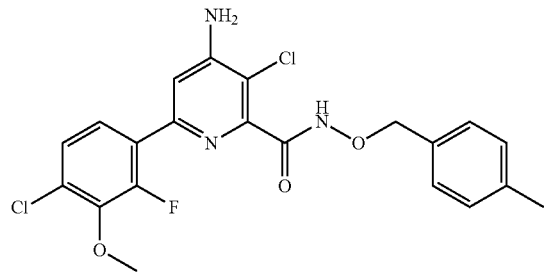 [SMILES: COc1c(Cl)ccc(-c2cc(N)c(Cl)c(C(=O)NOCc3ccc(C)cc3)n2)c1F]

The title compound (130 mg, 48%) was isolated as a white powder: mp 171-174° C.; $^1$H NMR (300 MHz, CDCl$_3$) δ 9.77 (br s, 1H), 7.47-7.37 (m, 4H), 7.24-7.19 (m, 3H), 5.05 (br s, 2H), 4.96 (br s, 2H), 4.00 (d, J=1 Hz, 3H), 2.40 (s, 3H); IR (neat film) 3467 (m), 3286 (m), 3180 (m), 2921 (w), 2851 (w), 1668 (s), 1630 (s) cm$^-$; ESIMS m/z 450.3 ([M+H]$^+$).

4-Amino-3-chloro-6-(4-chloro-2-fluoro-3-methoxyphenyl)-N-(4-chloro-benzyloxy)picolinamide (Compound 15)

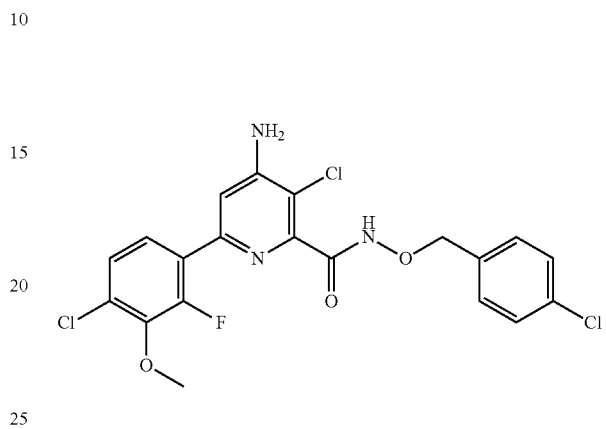

The title compound (130 mg, 46%) was isolated as a white powder: mp 177-180° C.; $^1$H NMR (300 MHz, CDCl$_3$) δ 9.81 (br s, 1H), 7.49-7.37 (m, 5H), 7.27-7.20 (m, 2H), 5.06 (br s, 2H), 4.97 (br s, 2H), 4.00 (d, J=1 Hz, 3H); IR (neat film) 3493 (m), 3382 (m), 3200 (m), 2924 (w), 1663 (s), 1624 (s); ESIMS m/z 470.2 ([M+H]$^+$).

4-Amino-3-chloro-6-(4-chloro-2-fluoro-3-methoxyphenyl)-N-((2R,3R,4S,5R,6R)-3,4,5-trimethoxy-6-(methoxymethyl)tetrahydro-2H-pyran-2-yloxy)picolinamide (Compound 16)

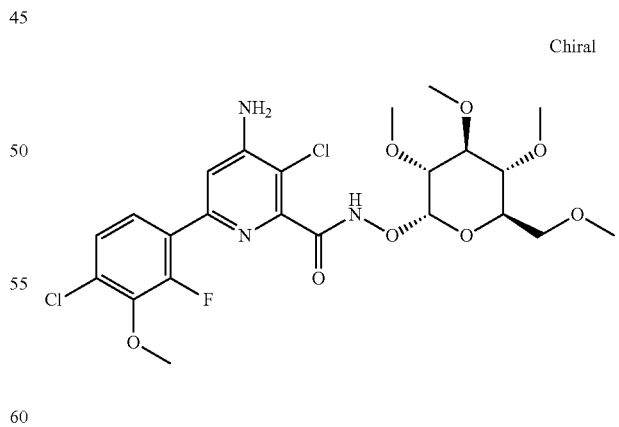

The title compound (190 mg, 56%) was isolated as a white powder: mp 184-187° C.; $^1$H NMR (300 MHz, CDCl$_3$) δ 10.00 (br s, 1H), 7.56 (dd, J=8, 9 Hz, 1H), 7.26-7.19 (m, 2H), 5.43 (d, J=3.5 Hz, 1H), 4.95 (br s, 2H), 4.13 (m, 1H), 3.99 (d, J=1 Hz, 3H), 3.69-3.60 (m, 8H), 3.58-3.52 (m, 4H), 3.42-3.34 (m, 4H), 3.25 (dd, J=9, 10 Hz, 1H); IR (neat film) 3475 (m), 3346 (m), 3225 (m), 2937 (m), 2833 (m), 1707 (s), 1628 (s) cm$^{-1}$; ESIMS m/z 564.3 ([M+H]$^+$).

4-Amino-3-chloro-6-(4-chloro-2-fluoro-3-methoxyphenyl)-N-(tetrahydrofuran-2-yloxy)picolinamide (Compound 17)

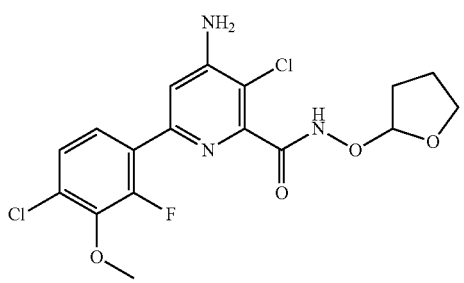 [SMILES: COc1c(Cl)ccc(-c2cc(N)c(Cl)c(C(=O)NOC3CCCO3)n2)c1F]

The title compound (140 mg, 56%) was isolated as a tan powder: mp 180-183° C.; $^1$H NMR (300 MHz, CDCl$_3$) δ 9.91 (br s, 1H), 7.57 (dd, J=8, 9 Hz, 1H), 7.26 (m, 1H), 7.19 (d, J=2 Hz, 1H), 5.56 (m, 1H), 4.93 (br s, 2H), 4.16-3.94 (m, 5H), 2.27-1.86 (m, 4H); IR (neat film) 3412 (w), 3325 (m), 3213 (w), 2950 (w), 2889 (w), 1679 (s), 1639 (s) cm$^{-1}$; ESIMS m/z 416.3 ([M+H]$^+$).

4-Amino-3-chloro-6-(4-chloro-2-fluoro-3-methoxyphenyl)-N-(cyclohex-2-enyl-oxy)picolinamide (Compound 18)

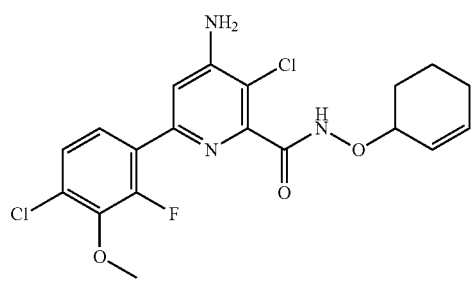 [SMILES: COc1c(Cl)ccc(-c2cc(N)c(Cl)c(C(=O)NOC3C=CCCC3)n2)c1F]

The title compound (170 mg, 44%) was isolated as a white powder: mp 180-182° C.; $^1$H NMR (300 MHz, CDCl$_3$) δ 9.79 (br s, 1H), 7.55 (t, J=8 Hz, 1H), 7.26 (dd, J=2, 8 Hz, 1H), 7.19 (d, J=2 Hz, 1H), 6.03 (m, 1H), 5.93 (m, 1H), 4.94 (br s, 2H), 4.57 (br s, 1H), 3.99 (d, J=1 Hz, 3H), 2.19-1.80 (m, 5H), 1.62 (m, 1H); IR (neat film) 3478 (w), 3330 (m), 3193 (m), 2937 (m), 1731 (w), 1651 (s), 1617 (s) cm$^{-1}$; ESIMS m/z 426.1 ([M+H]$^+$).

2-(4-Amino-3-chloro-6-(4-chloro-2-fluoro-3-methoxyphenyl)picolinamidooxy)acetic acid (Compound 19)

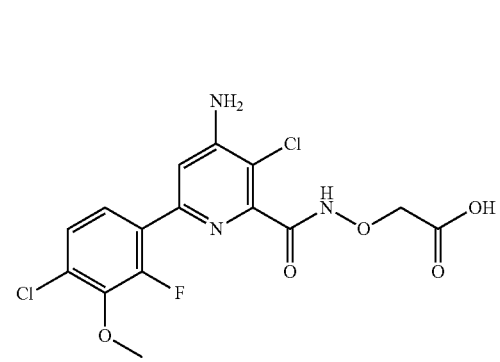 [SMILES: COc1c(Cl)ccc(-c2cc(N)c(Cl)c(C(=O)NOCC(=O)O)n2)c1F]

The title compound (170 mg, 71%) was isolated as a white powder: mp 189-191° C.; $^1$H NMR (300 MHz, DMSO-d$_6$) δ 7.67 (t, J=8 Hz, 1H), 7.41 (dd, J=1, 8 Hz, 1H), 7.21 (s, 1H), 6.77 (br s, 2H), 4.50 (s, 2H), 3.93 (d, J=1 Hz, 3H); IR (neat film) 3321 (m), 3208 (m), 2942 (w), 1730 (s), 1680 (s), 1643 (s) cm$^{-1}$; ESIMS m/z 404.2 ([M+H]$^+$).

4-Amino-3-chloro-6-(4-chloro-2-fluoro-3-methoxyphenyl)-N-phenoxypicolinamide (Compound 20)

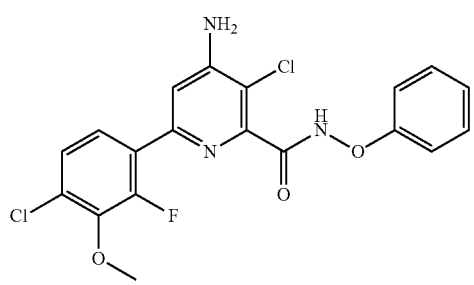 [SMILES: COc1c(Cl)ccc(-c2cc(N)c(Cl)c(C(=O)NOc3ccccc3)n2)c1F]

The title compound (100 mg, 38%) was isolated as a tan powder: mp 147-157° C. dec; $^1$H NMR (300 MHz, CDCl$_3$) δ 10.32 (br s, 1H), 7.55 (t, J=9 Hz, 1H), 7.36-7.15 (m, 6H), 7.06

(t, J=7 Hz, 1H), 5.00 (s, 2H), 4.00 (d, 3H); IR (neat film) 3487 (m), 3340 (m), 3225 (w), 2936 (w), 1664 (s), 1626 (s) cm$^{-1}$; ESIMS m/z 422.3 ([M+H]+).

4-Amino-N-tert-butoxy-3-chloro-6-(4-chloro-2-fluoro-3-methoxyphenyl)picolinamide (Compound 21)

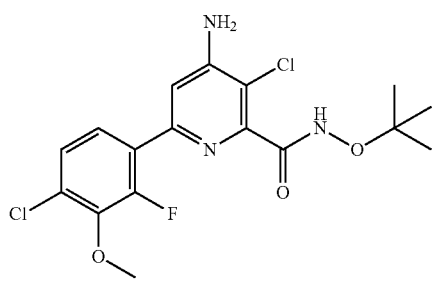 [SMILES: COc1c(Cl)ccc(-c2cc(N)c(Cl)c(C(=O)NOC(C)(C)C)n2)c1F]

The title compound (180 mg, 75%) was isolated as a white powder: mp 184-187° C.; $^1$H NMR (300 MHz, DMSO-d$_6$) δ 10.96 (br s, 1H), 7.66 (t, J=8 Hz, 1H), 7.43 (dd, J=2, 8 Hz, 1H), 7.20 (d, J=2 Hz, 1H), 6.75 (br s, 2H), 3.93 (d, J=1 Hz, 3H), 1.25 (s, 9H); IR (neat film) 3325 (w), 3196 (m), 2979 (m), 2940 (w), 1682 (s), 1632 (s) cm$^{-1}$; ESIMS m/z 402.3 ([M+H]$^+$).

4-Amino-3-chloro-6-(4-chloro-2-fluoro-3-methoxyphenyl)-N-(4-fluoro-benzyloxy)picolinamide (Compound 22)

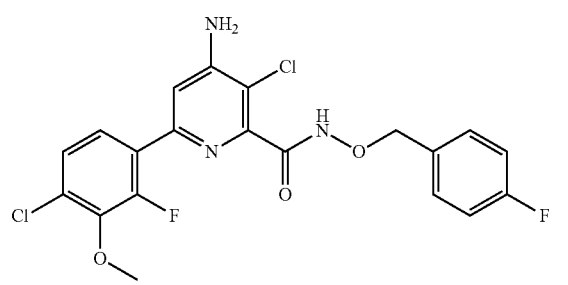 [SMILES: COc1c(Cl)ccc(-c2cc(N)c(Cl)c(C(=O)NOCc3ccc(F)cc3)n2)c1F]

The title compound (150 mg, 56%) was isolated as a yellow powder: mp 150-153° C.; $^1$H NMR (300 MHz, CDCl$_3$) δ 9.78 (br s, 1H), 7.47 (m, 2H), 7.39 (m, 1H), 7.24-7.18 (m, 2H), 7.08 (m, 2H), 5.03 (s, 2H), 4.95 (br s, 2H), 3.98 (d, J=1 Hz, 3H); IR (neat film) 3474 (m), 3364 (m), 3214 (m), 2941 (w), 1656 (s), 1624 (s) cm$^{-1}$; ESIMS m/z 454.3 ([M+H]$^+$).

4-Amino-3-chloro-6-(4-chloro-2-fluoro-3-methoxyphenyl)-N-(4-methoxy-benzyloxy)picolinamide (Compound 23)

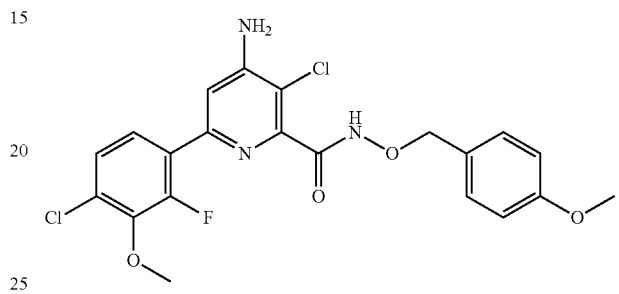

The title compound (190 mg, 70%) was isolated as an off-white powder: mp 142-145° C.; $^1$H NMR (300 MHz, CDCl$_3$) δ 9.72 (br s, 1H), 7.46-7.34 (m, 3H), 7.25-7.18 (m, 2H), 6.90 (m, 2H), 5.00 (s, 2H), 4.94 (br s, 2H), 3.97 (d, J=1 Hz, 3H), 3.82 (s, 3H); IR (neat film) 3479 (w), 3357 (m), 3200 (m), 2936 (w), 1654 (s), 1616 (s) cm$^{-1}$; ESIMS m/z 466.3 ([M+H]$^+$).

4-Amino-3-chloro-6-(4-chloro-2-fluoro-3-methoxyphenyl)-N-hydroxy-N-methylpicolinamide (Compound 24)

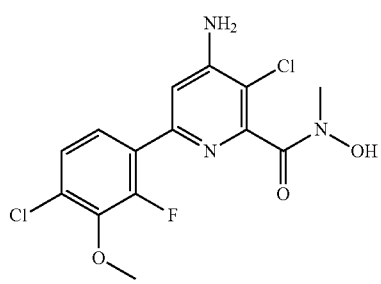 [SMILES: COc1c(Cl)ccc(-c2cc(N)c(Cl)c(C(=O)N(C)O)n2)c1F]

The title compound (95 mg, 33%) was isolated as a white powder: mp 211-214° C.; $^1$H NMR (300 MHz, DMSO-d$_6$) δ 10.04 (s, 1H), 7.59 (m, 1H), 7.41 (dd, J=1, 8 Hz, 1H), 7.14 (m, 1H), 6.65 (br s, 2H), 3.92 (s, 3H), 3.26 (s, 3H); IR (neat film) 3328 (w), 3198 (w), 2940 (w), 1646 (s), 1590 (s) cm$^{-1}$; ESIMS m/z 360.2 ([M+H]$^+$).

N-(2-Propenyloxy)-6-amino-5-chloro-2-(4-chloro-2-fluoro-3-methoxyphenyl)pyrimidine-4-carboxamide (Compound 25)

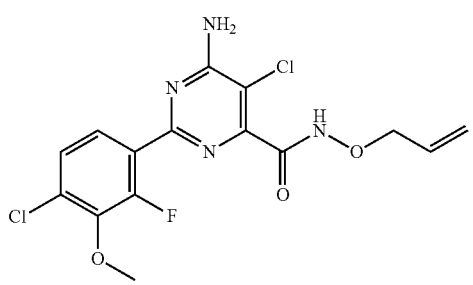 [SMILES: C=CCONC(=O)c1nc(-c2ccc(Cl)c(OC)c2F)nc(N)c1Cl]

The title compound (45 mg, 38%) was isolated as a white powder: mp 159-161° C.; $^1$H NMR (300 MHz, CDCl$_3$) δ 10.12 (br s, 1H), 7.68 (dd, J=8, 9 Hz, 1H), 7.24 (dd, J=2, 9 Hz, 1H), 6.07 (m, 1H), 5.74 (br s, 2H), 5.36-5.34 (m, 2H), 4.54 (d, J=6.5 Hz, 2H), 4.00 (d, J=1 Hz, 3H); IR (neat film) 3505 (w), 3365 (m), 3207 (w), 2942 (w), 1666 (s), 1624 (s) cm$^{-1}$; ESIMS m/z 387.2 ([M+H]$^+$).

N-(2-Propenyloxy)-4-amino-3-chloro-6-(4-chloro-2-fluoro-3-methoxyphenyl)-N-methylpicolinamide (Compound 26)

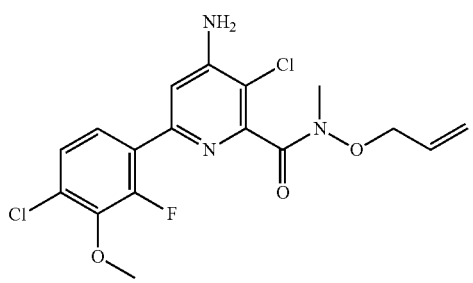 [SMILES: C=CCON(C)C(=O)c1nc(-c2ccc(Cl)c(OC)c2F)cc(N)c1Cl]

The title compound (100 mg, 42%) was isolated as a tan powder: mp 134-136° C.; $^1$H NMR (300 MHz, CDCl$_3$) δ 7.65 (dd, J=8, 9 Hz, 1H), 7.26 (m, 1H), 7.12 (d, J=2 Hz, 1H), 5.62 (m, 1H), 5.15-5.05 (m, 2H), 4.73 (br s, 2H), 4.34 (d, J=6 Hz, 2H), 3.97 (d, J=1 Hz, 3H), 3.43 (s, 3H); IR (neat film) 3445 (w), 3346 (w), 1670 (m), 1629 (m), 1589 (m) cm$^{-1}$; ESIMS m/z 400.3 ([M+H]$^+$).

N-(2-Propenyloxy)-4-amino-3,6-dichloropicolinamide (Compound 27)

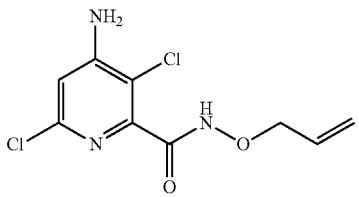 [SMILES: C=CCONC(=O)c1nc(Cl)cc(N)c1Cl]

The title compound (200 mg, 32%) was isolated as a light brown powder: mp 161-163° C.; $^1$H NMR (300 MHz, CDCl$_3$) δ 9.76 (br s, 1H), 6.74 (s, 1H), 6.05 (m, 1H), 5.46-5.32 (m, 2H), 5.00 (br s, 2H), 4.52 (d, J=6 Hz, 2H); IR (neat film) 3471 (m), 3336 (s), 3225 (s), 2920 (w), 1660 (s), 1620 (s) cm$^{-1}$; ESIMS m/z 262.1 ([M+H]$^+$).

4-Amino-3-chloro-6-(4-chloro-2-fluoro-3-methoxyphenyl)-N-(2-methyl-2-propenyl-oxy)picolinamide (Compound 28)

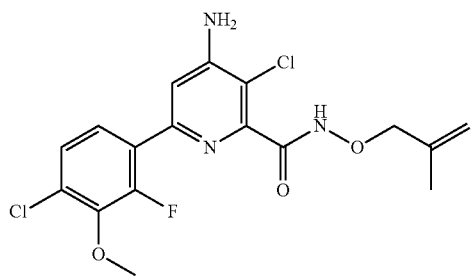

The title compound (95 mg, 26%) was isolated as an off-white powder: mp 147-149° C.; $^1$H NMR (300 MHz, CDCl$_3$) δ 9.83 (br s, 1H), 7.53 (t, J=8 Hz, 1H), 7.26 (m, 1H), 7.19 (d, J=2 Hz, 1H), 5.11-5.01 (m, 2H), 4.95 (br s, 2H), 4.46 (s, 2H), 3.99 (d, J=1 Hz, 3H), 1.88 (s, 3H); IR (neat film) 3475 (w), 3354 (m), 3203 (m), 2943 (w), 1654 (m), 1619 (s), 1584 (m) cm⁻; ESIMS m/z 400.3 ([M+H]⁺).

4-Amino-3-chloro-6-(4-chloro-2-fluoro-3-methoxyphenyl)-N-(2-chloro-2-propenyl-oxy)picolinamide (Compound 29)

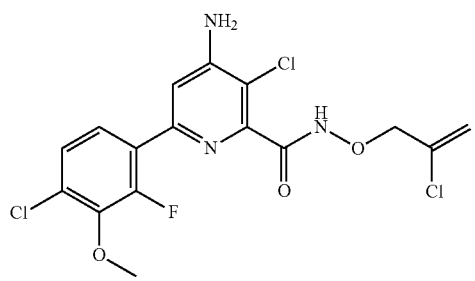

The title compound (200 mg, 53%) was isolated as a white powder: mp 146-148° C.; ¹H NMR (300 MHz, CDCl₃) δ 9.97 (br s, 1H), 7.53 (t, J=8 Hz, 1H), 7.26 (m, 1H), 7.20 (d, J=2 Hz, 1H), 5.59 (m, 1H), 5.51 (d, J=2 Hz, 1H), 4.95 (br s, 2H), 4.65 (s, 2H), 3.99 (d, J=1 Hz, 3H); IR (neat film) 3487 (w), 3380 (m), 3153 (w), 2937 (w), 1662 (s), 1622 (s), 1587 (m) cm⁻¹; ESIMS m/z 420.1 ([M+H]⁺).

(E)-4-Amino-N-(2-butenyloxy)-3-chloro-6-(4-chloro-2-fluoro-3-methoxy-phenyl)picolinamide (Compound 30)

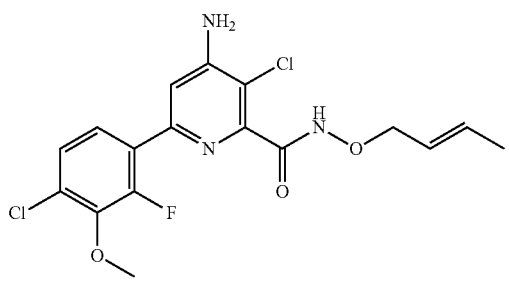 [SMILES: C/C=C/CONC(=O)c1nc(-c2ccc(Cl)c(OC)c2F)cc(N)c1Cl]

The title compound (190 mg, 53%) was isolated as a white powder: mp 154-156° C.; ¹H NMR (300 MHz, CDCl₃) δ 9.79 (br s, 1H), 7.54 (t, J=8 Hz, 1H), 7.26 (m, 1H), 7.20 (d, J=2 Hz, 1H), 5.88 (m, 1H), 5.72 (m, 1H), 4.94 (br s, 2H), 4.46 (d, J=7 Hz, 2H), 3.99 (d, J=1 Hz, 3H), 1.75 (d, J=6 Hz, 3H); IR (neat film) 3454 (w), 3339 (m), 3285 (m), 3190 (m), 2942 (w), 1681 (s), 1627 (s), 1585 (s) cm⁻¹; ESIMS m/z 400.1 ([M+H]⁺).

(E)-4-Amino-3-chloro-6-(4-chloro-2-fluoro-3-methoxyphenyl)-N-(3-chloro-2-propenyl-oxy)picolinamide (Compound 31)

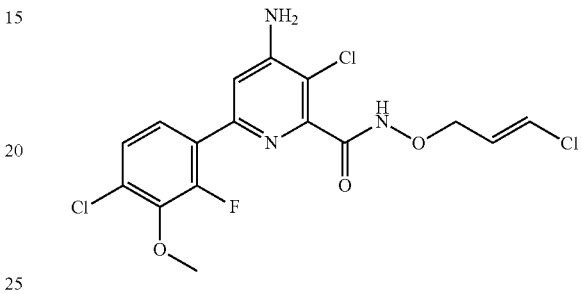

The title compound (210 mg, 55%) was isolated as a white powder: mp 163-165° C.; ¹H NMR (300 MHz, CDCl₃) δ 9.86 (br s, 1H), 7.53 (t, J=8 Hz, 1H), 7.26 (m, 1H), 7.20 (d, J=2 Hz, 1H), 6.40 (m, 1H), 6.18 (m, 1H), 4.96 (br s, 2H), 4.53 (d, J=7 Hz, 2H), 3.99 (d, J=1 Hz, 3H); IR (neat film) 3480 (w), 3322 (w), 3266 (w), 3199 (w), 1679 (m), 1623 (m), 1587 (m) cm⁻¹; ESIMS m/z 420.1 ([M+H]⁺).

4-Amino-3-chloro-6-(4-chloro-2-fluoro-3-methoxyphenyl)-N-(cyclopropyl-methoxy)picolinamide (Compound 32)

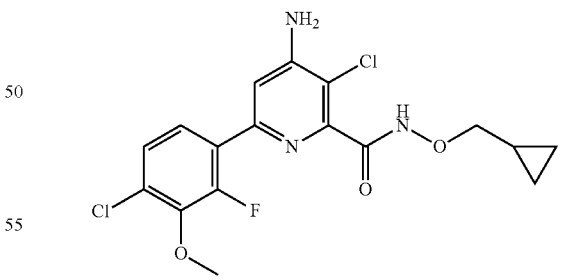

The title compound (230 mg, 61%) was isolated as a white powder: mp 164-166° C.; ¹H NMR (300 MHz, CDCl₃) δ 9.92 (br s, 1H), 7.54 (t, J=8 Hz, 1H), 7.26 (dd, J=2, 8 Hz, 1H), 7.19 (d, J=2 Hz, 1H), 4.95 (br s, 2H), 3.99 (s, 3H), 3.89 (d, J=7 Hz, 2H), 1.22 (m, 1H), 0.62 (m, 2H), 0.36 (m, 2H); IR (neat film)

3488 (m), 3295 (m), 3197 (w), 3024 (w), 2976 (w), 2945 (w), 1675 (s), 1626 (m), 1589 (m) cm$^{-1}$; ESIMS m/z 400.1 ([M+H]$^+$).

4-Amino-N-(but-3-en-2-yloxy)-3-chloro-6-(4-chloro-2-fluoro-3-methoxy-phenyl)picolinamide (Compound 33)

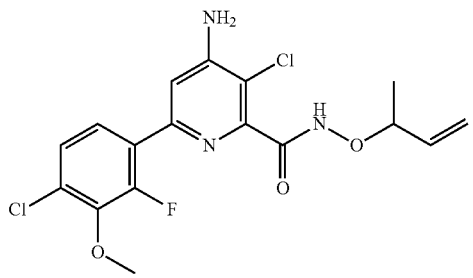 [SMILES: C=CC(C)ONC(=O)c1nc(-c2ccc(Cl)c(OC)c2F)cc(N)c1Cl]

The title compound (160 mg, 44%) was isolated as a white powder: mp 176-179° C.; $^1$H NMR (300 MHz, CDCl$_3$) δ 9.72 (br s, 1H), 7.52 (t, J=8 Hz, 1H), 7.26 (m, 1H), 7.19 (d, J=2 Hz, 1H), 5.92 (m, 1H), 5.36-5.25 (m, 2H), 4.93 (br s, 2H), 4.55 (m, 1H), 3.98 (d, J=1 Hz, 3H), 1.43 (d, J=6 Hz, 3H); IR (neat film) 3479 (w), 3332 (m), 3197 (m), 2983 (w), 2939 (w), 1653 (s), 1619 (s) cm$^{-1}$; ESIMS m/z 400.1 ([M+H]$^+$).

4-Amino-3,6-dichloro-N-(4-fluorobenzyloxy)picolinamide (Compound 34)

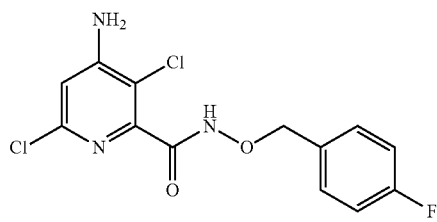 [SMILES: Nc1cc(Cl)nc(C(=O)NOCc2ccc(F)cc2)c1Cl]

The title compound (400 mg, 50%) was isolated as an off-white powder: mp 209-211° C.; $^1$H NMR (300 MHz, CDCl$_3$) δ 9.72 (br s, 1H), 7.47 (m, 2H), 7.07 (m, 2H), 6.71 (s, 1H), 5.02-4.95 (m, 4H); IR (neat film) 3467 (s), 3319 (s), 3255 (m), 1656 (s), 1615 (s) cm$^{-1}$; ESIMS m/z 327.8 ([M−H]$^-$).

N-(2-Propenyloxy)-6-amino-2-(4-chloro-2-fluoro-3-methoxyphenyl)-5-methoxypyrimidine-4-carboxamide (Compound 35)

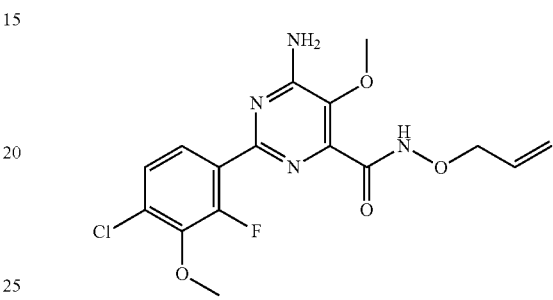

The title compound (130 mg, 68%) was isolated as a white powder: mp 148-150° C.; $^1$H NMR (300 MHz, CDCl$_3$) δ 10.15 (br s, 1H), 7.64 (dd, J=8, 9 Hz, 1H), 7.22 (dd, J=2, 9 Hz, 1H), 6.07 (m, 1H), 5.54-5.43 (m, 3H), 5.36 (m, 1H), 4.53 (d, J=7 Hz, 2H), 4.03 (s, 3H), 4.00 (s, 3H); IR (neat film) 3502 (m), 3365 (m), 3322 (m), 3215 (w), 3172 (w), 2951 (w), 1692 (s), 1621 (s) cm$^{-1}$; ESIMS m/z 383.1 ([M−H]$^-$).

4-Amino-3-chloro-6-(4-chloro-2-fluoro-3-methoxyphenyl)-N-(thiazol-5-yl-methoxy)picolinamide (Compound 36)

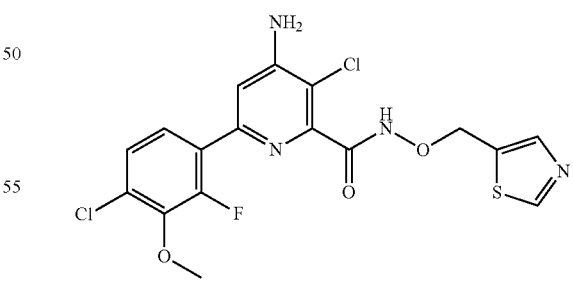

The title compound (120 mg, 44%) was isolated as a white powder: mp 179-181° C.; $^1$H NMR (300 MHz, CDCl$_3$) δ 9.88 (br s, 1H), 8.87 (s, 1H), 7.94 (s, 1H), 7.45 (t, J=8 Hz, 1H), 7.26 (m, 1H), 7.19 (d, J=2 Hz, 1H), 5.31 (s, 2H), 4.96 (br s, 2H), 3.98 (s, 3H); IR (neat film) 3377 (w), 3323 (w), 3244 (m), 3214 (s), 3085 (w), 2939 (w), 1684 (s), 1646 (s), 1590 (m) cm$^{-1}$; ESIMS m/z 443.1 ([M+H]$^+$).

4-Amino-3-chloro-6-(4-chloro-2-fluoro-3-methoxyphenyl)-N-(2-fluoro-2-propenyl-oxy)picolinamide (Compound 37)

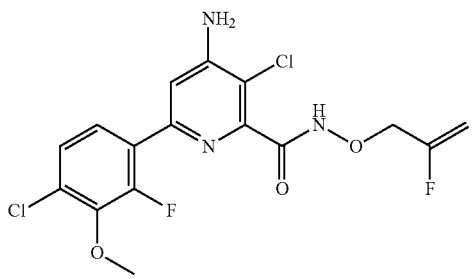 [SMILES: C=C(F)CONC(=O)c1nc(-c2ccc(Cl)c(OC)c2F)cc(N)c1Cl]

The title compound (120 mg, 50%) was isolated as a white powder: mp 172-174° C.; $^1$H NMR (300 MHz, CDCl$_3$) δ 10.00 (br s, 1H), 7.53 (dd, J=8, 9 Hz, 1H), 7.26 (m, 1H), 7.21 (d, J=2 Hz, 1H), 4.96 (br s, 2H), 4.90 (dd, J=3, 16 Hz, 1H), 4.71 (dd, J=3, 47 Hz, 1H), 4.58 (d, J=17 Hz, 2H), 3.99 (d, J=1 Hz, 3H); IR (neat film) 3497 (w), 3383 (s), 3193 (w), 2940 (w), 1662 (m), 1629 (s), 1587 (m) cm$^{-1}$; ESIMS m/z 404.1 ([M+H]$^+$).

4-Amino-N-(3-butenyloxy)-3-chloro-6-(4-chloro-2-fluoro-3-methoxyphenyl)picolinamide (Compound 38)

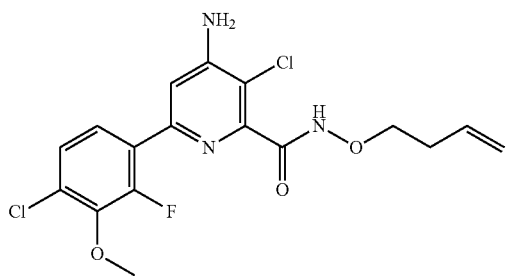 [SMILES: C=CCCONC(=O)c1nc(-c2ccc(Cl)c(OC)c2F)cc(N)c1Cl]

The title compound (120 mg, 50%) was isolated as a white powder: mp 141-143° C.; $^1$H NMR (300 MHz, CDCl$_3$) δ 9.90 (br s, 1H), 7.53 (dd, J=8, 9 Hz, 1H), 7.26 (m, 1H), 7.19 (d, J=2 Hz, 1H), 5.89 (m, 1H), 5.23-5.07 (m, 2H), 4.95 (br s, 2H), 4.12 (t, J=7 Hz, 2H), 3.99 (d, J=1 Hz, 3H), 2.51 (m, 2H); IR (neat film) 3497 (w), 3464 (w), 3383 (m), 3362 (w), 3191 (w), 3005 (w), 2944 (w), 1712 (s), 1681 (m), 1629 (s), 1587 (m) cm$^{-1}$; ESIMS m/z 400.1 ([M+H]$^+$).

N-(2-Propenyloxy)-4-amino-3-chloro-6-(4-chloro-2-fluoro-3-methoxyphenyl)-5-fluoropicolinamide (Compound 39)

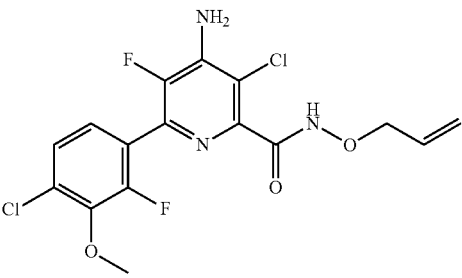 [SMILES: C=CCONC(=O)c1nc(-c2ccc(Cl)c(OC)c2F)c(F)c(N)c1Cl]

The title compound (73 mg, 66%) was isolated as a white powder: mp 184-186° C.; $^1$H NMR (300 MHz, CDCl$_3$) δ 9.79 (br s, 1H), 7.29 (dd, J=2, 9 Hz, 1H), 7.18 (dd, J=7, 9 Hz, 1H), 6.04 (m, 1H), 5.43-5.30 (m, 2H), 5.03 (br s, 2H), 4.52 (d, J=6 Hz, 2H), 4.01 (d, J=1 Hz, 3H); IR (neat film) 3491 (w), 3396 (m), 3304 (m), 3189 (w), 2994 (w), 2951 (w), 1681 (m), 1656 (s), 1622 (s) cm$^{-1}$; ESIMS m/z 404.0 ([M+H]$^+$).

(4-Amino-3-chloro-6-(4-chloro-2-fluoro-3-methoxyphenyl)pyridin-2-yl)(isoxazolidin-2-yl)methanone (Compound 40)

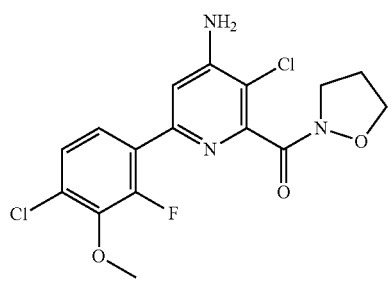 [SMILES: COc1c(Cl)ccc(-c2cc(N)c(Cl)c(C(=O)N3CCCO3)n2)c1F]

The title compound (110 mg, 48%) was isolated as a white powder: mp 204-207° C.; $^1$H NMR (300 MHz, CDCl$_3$) δ 7.66 (t, J=8 Hz, 1H), 7.20 (dd, J=2, 8 Hz, 1H), 7.13 (d, J=2 Hz, 1H), 4.75 (br s, 2H), 4.03-3.92 (m, 7H), 2.42 (p, J=7 Hz, 2H); IR (neat film) 3430 (w), 3329 (m), 3216 (m), 2939 (w), 2888 (w), 1629 (s), 1588 (s) cm$^{-1}$; ESIMS m/z 386.1 ([M+H]$^+$).

4-Amino-3-chloro-6-(4-chloro-2-fluoro-3-methoxyphenyl)-N-((2-chlorothiazol-5-yl)-methoxy)picolinamide (Compound 41)

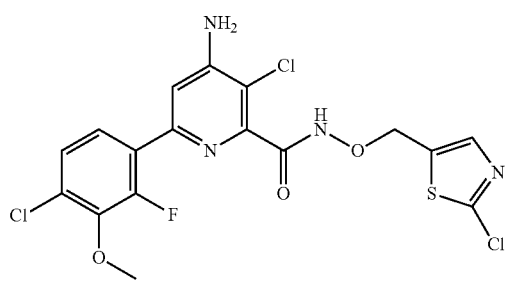 [SMILES: COc1c(Cl)ccc(-c2cc(N)c(Cl)c(C(=O)NOCc3cnc(Cl)s3)n2)c1F]

The title compound (90 mg, 31%) was isolated as a white powder: mp 164-167° C.; $^1$H NMR (300 MHz, CDCl$_3$) δ 9.90 (br s, 1H), 7.57 (s, 1H), 7.46 (t, J=8 Hz, 1H), 7.26 (m, 1H), 7.20 (d, J=2 Hz, 1H), 5.19 (s, 2H), 4.98 (br s, 2H), 3.99 (d, J=1 Hz, 3H); IR (neat film) 3472 (w), 3337 (m), 3199 (m), 3003 (w), 2942 (w), 1666 (s), 1628 (m), 1585 (m) cm$^{-1}$; ESIMS m/z 477.0 ([M+H]$^+$).

4-Amino-3-chloro-6-(4-chloro-2-fluoro-3-methoxyphenyl)-N-(furan-2-yl-methoxy)picolinamide (Compound 42)

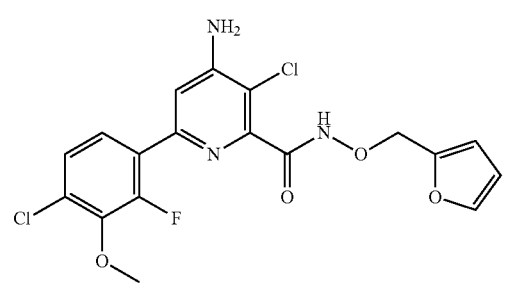 [SMILES: COc1c(Cl)ccc(-c2cc(N)c(Cl)c(C(=O)NOCc3ccco3)n2)c1F]

The title compound (170 mg, 65%) was isolated as a white powder: mp 161-164° C.; $^1$H NMR (300 MHz, CDCl$_3$) δ 9.85 (br s, 1H), 7.43 (m, 2H), 7.25-7.20 (m, 2H), 6.51 (d, J=3 Hz, 1H), 6.39 (dd, J=2, 3 Hz, 1H), 5.03 (s, 2H), 4.95 (br s, 2H), 3.98 (d, J=1 Hz, 3H); IR (neat film) 3475 (w), 3292 (m), 3191 (m), 2948 (w), 1670 (s), 1627 (s), 1582 (s) cm$^{-1}$; ESIMS m/z 426.1 ([M+H]$^+$).

4-Amino-3-chloro-6-(4-chloro-2-fluoro-3-methoxyphenyl)-N-(furan-3-yl-methoxy)picolinamide (Compound 43)

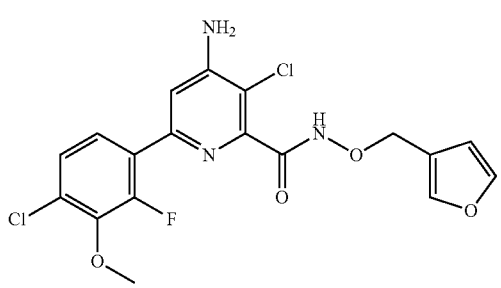 [SMILES: COc1c(Cl)ccc(-c2cc(N)c(Cl)c(C(=O)NOCc3ccoc3)n2)c1F]

The title compound (120 mg, 46%) was isolated as a white powder: mp 160-162° C.; $^1$H NMR (300 MHz, CDCl$_3$) δ 9.78 (br s, 1H), 7.55 (s, 1H), 7.49-7.42 (m, 2H), 7.24 (dd, J=8, 2 Hz, 1H), 7.19 (d, J=2 Hz, 1H), 6.57 (s, 1H), 4.97-4.92 (m, 4H), 3.98 (d, J=1 Hz, 3H); IR (neat film) 3472 (m), 3317 (w), 3267 (m), 3206 (w), 1685 (m), 1636 (m), 1590 (m) cm$^{-1}$; ESIMS m/z 426.1 ([M+H]$^+$).

4-Amino-3-chloro-6-(4-chloro-2-fluoro-3-methoxyphenyl)-N-(cyclohexenyl-methoxy)picolinamide (Compound 44)

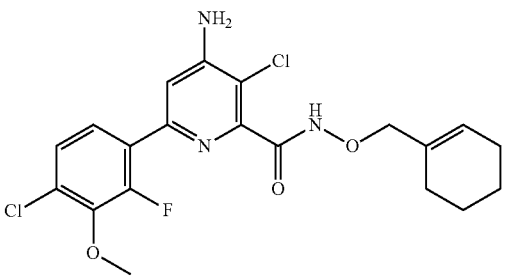 [SMILES: COc1c(Cl)ccc(-c2cc(N)c(Cl)c(C(=O)NOCC3=CCCCC3)n2)c1F]

The title compound (150 mg, 38%) was isolated as a tan powder: $^1$H NMR (300 MHz, CDCl$_3$) δ 9.77-9.63 (m, 1H), 7.54 (m, 1H), 7.27-7.17 (m, 2H), 5.86-4.35 (m, 5H), 3.99 (m, 3H), 2.18 (m, 2H), 2.05 (m, 2H), 1.73-1.57 (m, 4H); IR (neat film) 3472 (w), 3341 (m), 3218 (m), 2934 (m), 1709 (s), 1678 (s), 1626 (s), 1586 (s) cm$^{-1}$; ESIMS m/z 438.0 ([M−H]$^-$).

(E)-4-Amino-3-chloro-6-(4-chloro-2-fluoro-3-methoxyphenyl)-N-(2-pentenyl-oxy)picolinamide (Compound 45)

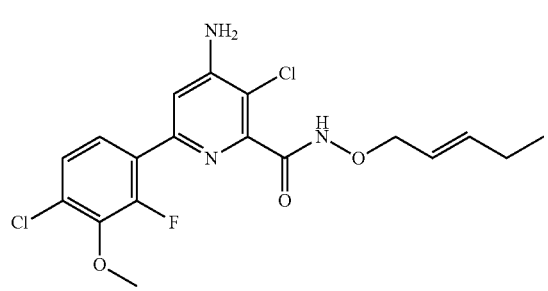 [SMILES: CC/C=C/CONC(=O)c1nc(-c2ccc(Cl)c(OC)c2F)cc(N)c1Cl]

The title compound (300 mg, 79%) was isolated as a white powder: mp 145-147° C.; $^1$H NMR (300 MHz, CDCl$_3$) δ 9.81 (s, 1H), 7.53 (t, J=8 Hz, 1H), 7.27-7.17 (m, 2H), 5.91 (m, 1H), 5.69 (m, 1H), 4.94 (br s, 2H), 4.48 (d, J=7 Hz, 2H), 3.99 (d, J=1 Hz, 3H), 2.10 (p, J=7 Hz, 2H), 1.00 (t, J=7 Hz, 3H); IR (neat film) 3480 (w), 3346 (m), 3200 (m), 2966 (m), 2937 (m), 1655 (s), 1622 (s), 1585 (s) cm$^{-1}$; ESIMS m/z 412.2 ([M−H]$^-$).

4-Amino-N-butoxy-3-chloro-6-(4-chloro-2-fluoro-3-methoxyphenyl)picolinamide (Compound 46)

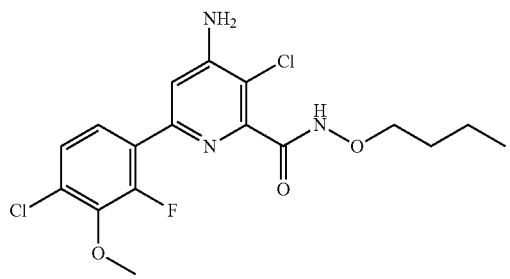 [SMILES: CCCCONC(=O)c1nc(-c2ccc(Cl)c(OC)c2F)cc(N)c1Cl]

The title compound (210 mg, 58%) was isolated as a white powder: mp 130-132° C.; $^1$H NMR (300 MHz, CDCl$_3$) δ 9.85 (s, 1H), 7.54 (t, J=8 Hz, 1H), 7.27 (dd, J=8, 2 Hz, 1H), 7.18 (d, J=2 Hz, 1H), 4.94 (br s, 2H), 4.06 (t, J=7 Hz, 2H), 3.99 (d, J=1 Hz, 3H), 1.72 (m, 2H), 1.47 (m, 2H), 0.96 (t, J=7 Hz, 3H); IR (neat film) 3478 (m), 3269 (m), 3188 (w), 2962 (w), 2874 (w), 1683 (s), 1623 (m) cm$^{-1}$; ESIMS m/z 402.1 ([M+H]$^+$).

4-Amino-3-chloro-N-((5-chloro-1,2,3-thiadiazol-4-yl)methoxy)-6-(4-chloro-2-fluoro-3-methoxyphenyl)picolinamide (Compound 47)

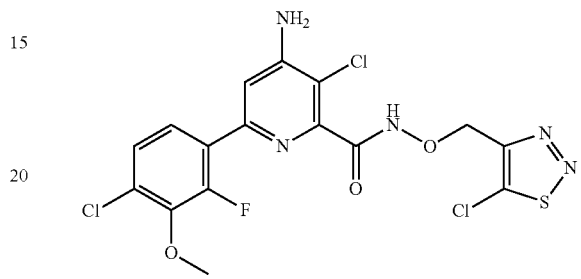

The title compound (180 mg, 78%) was isolated as a white powder: mp 179-181° C.; $^1$H NMR (300 MHz, DMSO-d$_6$) δ 7.70 (t, J=8 Hz, 1H), 7.42 (dd, J=9, 2 Hz, 1H), 7.22 (d, J=2 Hz, 1H), 6.77 (br s, 2H), 5.31 (s, 2H), 3.92 (s, 3H); IR (neat film) 3455 (s), 3364 (s), 3296 (m), 3245 (m), 2996 (w), 2950 (w), 1701 (m), 1638 (m), 1587 (w) cm$^{-1}$; ESIMS m/z 480.1 ([M+H]$^+$).

4-Amino-3-chloro-6-(4-chloro-2-fluoro-3-methoxyphenyl)-5-fluoro-N-(tetrahydro-2H-pyran-2-yloxy)picolinamide (Compound 48)

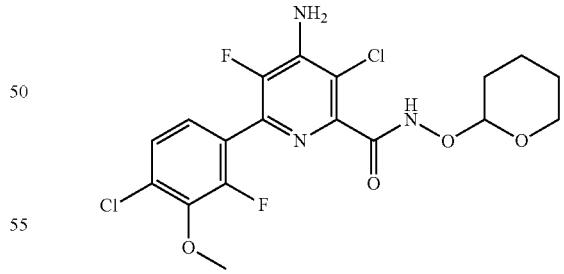

The title compound (210 mg, 81%) was isolated as a white powder: mp 177-180° C.; $^1$H NMR (300 MHz, CDCl$_3$) δ 9.91 (s, 1H), 7.30 (dd, J=9, 2 Hz, 1H), 7.20 (dd, J=9, 7 Hz, 1H), 5.10 (br t, J=3 Hz, 1H), 5.02 (br s, 2H), 4.06 (m, 1H), 4.00 (d, J=1 Hz, 3H), 3.64 (m, 1H), 1.97-1.79 (m, 3H), 1.68-1.52 (m, 3H); IR (neat film) 3419 (m), 3331 (s), 3232 (m), 2944 (m), 2868 (w), 1688 (w), 1627 (s) cm⁻¹; ESIMS m/z 446.0 ([M−H]⁻).

4-Amino-3-chloro-6-(4-chloro-2-fluoro-3-methoxyphenyl)-N-(2-methoxy-ethoxy)picolinamide (Compound 49)

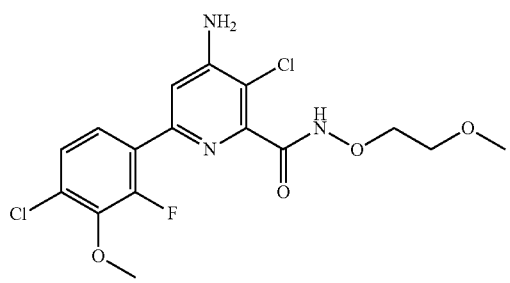 [SMILES: COCCONC(=O)c1nc(-c2ccc(Cl)c(OC)c2F)cc(N)c1Cl]

The title compound (180 mg, 75%) was isolated as a white powder: mp 155-157° C.; ¹H NMR (300 MHz, CDCl₃) δ 10.21 (br s, 1H), 7.58 (dd, J=9, 8 Hz, 1H), 7.28-7.21 (m, 2H), 4.94 (br s, 2H), 4.23 (m, 2H), 3.99 (d, J=1 Hz, 3H), 3.73 (m, 2H), 3.44 (s, 3H); IR (neat film) 3434 (m), 3352 (s), 3197 (m), 2940 (m), 2894 (w), 1661 (m), 1640 (m), 1587 (m) cm⁻¹; ESIMS m/z 404.1 ([M+H]⁺).

4-Amino-3-chloro-6-(4-chloro-2-fluoro-3-methoxyphenyl)-N-(2-cyanoethoxy)picolinamide (Compound 50)

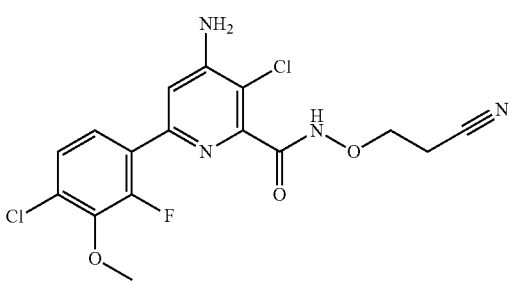 [SMILES: COc1c(Cl)ccc(-c2cc(N)c(Cl)c(C(=O)NOCCC#N)n2)c1F]

The title compound (160 mg, 67%) was isolated as a white powder: mp 191-194° C.; ¹H NMR (300 MHz, CDCl₃) δ 10.09 (br s, 1H), 7.54 (t, J=8 Hz, 1H), 7.26-7.17 (m, 2H), 4.98 (br s, 2H), 4.31 (t, J=7 Hz, 2H), 4.00 (s, 3H), 2.84 (t, J=7 Hz, 2H); IR (neat film) 3494 (m), 3469 (m), 3355 (s), 3231 (m), 2940 (w), 2255 (w), 1695 (m), 1628 (m), 1586 (m) cm⁻¹; ESIMS m/z 399.1 ([M+H]⁺).

4-Amino-3-chloro-6-(4-chloro-2-fluoro-3-methoxyphenyl)-N-((2-methoxyethoxy)-methoxy)picolinamide (Compound 51)

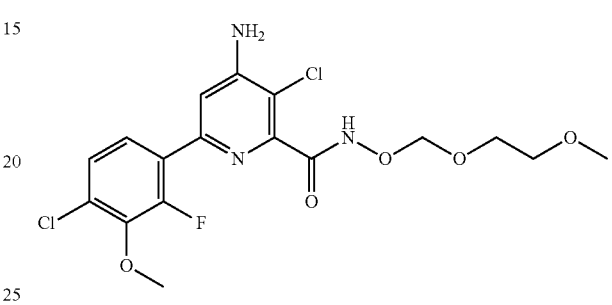

The title compound (250 mg, 64%) was isolated as a white powder: mp 126-128° C.; ¹H NMR (300 MHz, CDCl₃) δ 10.32 (s, 1H), 7.63 (dd, J=9, 8 Hz, 1H), 7.25 (dd, J=8, 2 Hz, 1H), 7.20 (d, J=2 Hz, 1H), 5.05 (s, 2H), 4.92 (br s, 2H), 3.98 (d, J=1 Hz, 3H), 3.94 (m, 2H), 3.60 (m, 2H), 3.31 (s, 3H); IR (neat film) 3460 (m), 3343 (s), 3224 (s), 3194 (s), 2979 (m), 2939 (m), 2883 (m), 1689 (m), 1628 (m), 1586 (m) cm⁻¹; ESIMS m/z 434.2 ([M+H]⁺).

(4-Amino-3-chloro-6-(4-chloro-2-fluoro-3-methoxyphenyl)pyridin-2-yl)(3,6-dihydro-2H-1,2-oxazin-2-yl)methanone (Compound 52)

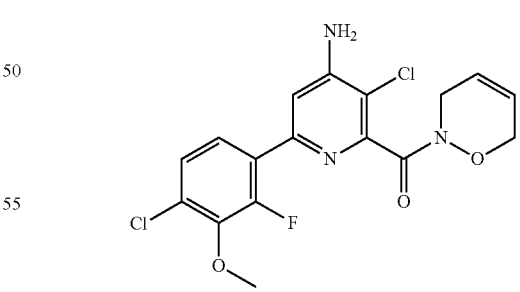

The title compound (95 mg, 40%) was isolated as a light brown powder: mp 78-81° C.; ¹H NMR (300 MHz, CDCl₃) δ 7.66 (dd, J=9, 8 Hz, 1H), 7.21 (dd, J=9, 2 Hz, 1H), 7.14 (d, J=2 Hz, 1H), 5.90 (br s, 2H), 4.74 (br s, 2H), 4.46 (m, 2H), 4.42 (m, 2H), 3.98 (d, J=1 Hz, 3H); IR (neat film) 3441 (s), 3341

(s), 3224 (m), 2943 (w), 2903 (w), 2854 (w), 1640 (s), 1591 (m) cm$^{-1}$; ESIMS m/z 398.2 ([M+H]$^+$).

N-(2-Propenyloxy)-4-amino-3-chloro-6-(4-methylphenyl)picolinamide (Compound 53)

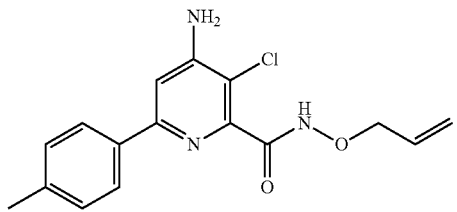 [SMILES: C=CCONC(=O)c1nc(-c2ccc(C)cc2)cc(N)c1Cl]

The title compound (140 mg, 78%) was isolated as a white powder: mp 177-179° C.; $^1$H NMR (300 MHz, CDCl$_3$) δ 10.03 (br s, 1H), 7.76 (d, J=8 Hz, 2H), 7.26 (d, J=8 Hz, 2H), 7.11 (s, 1H), 6.08 (m, 1H), 5.46-5.33 (m, 2H), 4.88 (br s, 2H), 4.55 (d, J=7 Hz, 2H), 2.41 (s, 3H); IR (neat film) 3478 (m), 3347 (s), 3208 (m), 3020 (w), 2985 (w), 2925 (w), 2871 (w), 1655 (s), 1623 (s) cm$^{-1}$; ESIMS m/z 318.1 ([M+H]$^+$).

N-(2-Propenyloxy)-4-amino-3-chloro-6-(benzo[d][1,3]dioxol-5-yl)-3-chloropicolinamide (Compound 54)

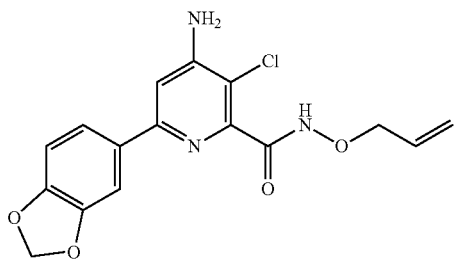 [SMILES: C=CCONC(=O)c1nc(-c2ccc3c(c2)OCO3)cc(N)c1Cl]

The title compound (140 mg, 78%) was isolated as a white powder: mp 168-171° C.; $^1$H NMR (300 MHz, CDCl$_3$) δ 9.97 (br s, 1H), 7.39-7.34 (m, 2H), 7.04 (s, 1H), 6.88 (d, J=9 Hz, 1H), 6.15-5.98 (m, 3H), 5.46-5.34 (m, 2H), 4.87 (br s, 2H), 4.55 (d, J=7 Hz, 2H); IR (neat film) 3477 (m), 3345 (s), 3224 (m), 2926 (w), 1653 (m), 1625 (m) cm$^{-1}$; ESIMS m/z 348.1 ([M+H]$^+$).

N-(2-Propenyloxy)-4-amino-3-chloro-6-(4-fluorophenyl)picolinamide (Compound 55)

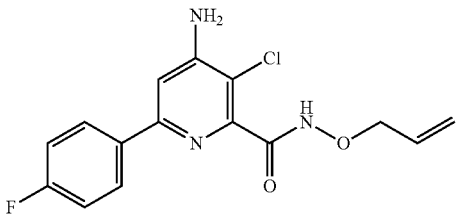 [SMILES: C=CCONC(=O)c1nc(-c2ccc(F)cc2)cc(N)c1Cl]

The title compound (130 mg, 72%) was isolated as a white powder: mp 182-185° C.; $^1$H NMR (300 MHz, CDCl$_3$) δ 9.94 (br s, 1H), 7.85 (m, 2H), 7.14 (m, 2H), 7.09 (s, 1H), 6.08 (m, 1H), 5.46-5.33 (m, 2H), 4.92 (br s, 2H), 4.55 (d, J=7 Hz, 2H); IR (neat film) 3479 (m), 3345 (s), 3221 (s), 2986 (w), 2937 (w), 1656 (s), 1625 (s) cm$^{-1}$; ESIMS m/z 322.1 ([M+H]$^+$).

N-(2-Propenyloxy)-4-amino-3-chloro-6-(4-cyanophenyl)picolinamide (Compound 56)

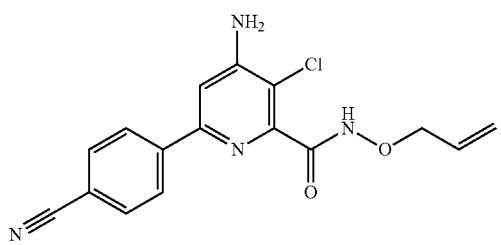 [SMILES: C=CCONC(=O)c1nc(-c2ccc(C#N)cc2)cc(N)c1Cl]

The title compound (90 mg, 75%) was isolated as a white powder: mp 218-221° C.; $^1$H NMR (300 MHz, CDCl$_3$) δ 9.84 (br s, 1H), 7.98 (d, J=8 Hz, 2H), 7.75 (d, J=8 Hz, 2H), 7.16 (s, 1H), 6.08 (m, 1H), 5.46-5.33 (m, 2H), 4.99 (br s, 2H), 4.56 (d, J=6 Hz, 2H); IR (neat film) 3470 (m), 3287 (s), 3187 (m), 2933 (w), 2227 (m), 1677 (m), 1620 (m) cm$^{-1}$; ESIMS m/z 329.1 ([M+H]$^+$).

Example 11

Preparation of 4-amino-3-chloro-6-(4-chloro-2-fluoro-3-methoxyphenyl)-N-hydroxypicolinamide (Compound 57)

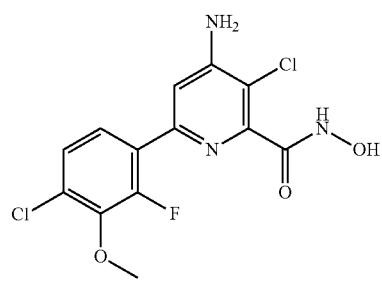 [SMILES: COc1c(Cl)ccc(-c2cc(N)c(Cl)c(C(=O)NO)n2)c1F]

A 50% aq solution of hydroxylamine (4.4 mL, 72 mmol, 50 equiv) was added to a stirred suspension of methyl 4-amino-3-chloro-6-(4-chloro-2-fluoro-3-methoxyphenyl)picolinate (500 mg, 1.4 mmol, 1.0 equiv) in 1,2-dimethoxyethane (1.0 mL) at 23° C. The resulting white suspension was stirred at 23° C. for 4 days (d). The reaction mixture was concentrated by rotary evaporation to afford a white powder (500 mg, 99%): mp 166-169° C.; $^1$H NMR (300 MHz, DMSO-d$_6$) δ 9.19 (br s, 1H), 7.68 (t, J=8 Hz, 1H), 7.42 (m, 1H), 7.20 (m, 1H), 6.73 (br s, 2H), 6.53 (br s, 1H), 3.93 (s, 3H); IR (neat film) 3322 (m), 2941 (w), 2878 (w), 1653 (s), 1632 (s) cm$^{-1}$; ESIMS m/z 346.2 ([M+H]$^+$).

Other compounds prepared from known or previously described starting materials by the method of Example 11 above include:

6-Amino-2-(4-chloro-2,3-difluorophenyl)-N-hydroxy-5-methoxypyrimidine-4-carboxamide (Compound 58)

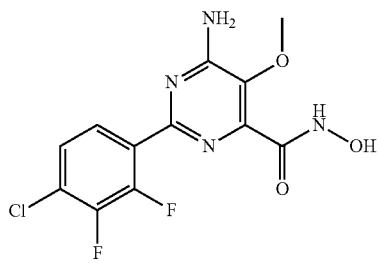 [SMILES: COc1c(N)nc(-c2ccc(Cl)c(F)c2F)nc1C(=O)NO]

The title compound (78 mg, 81%) was isolated as an off-white powder: mp 192-194° C.; $^1$H NMR (300 MHz, DMSO-$d_6$) δ 9.25 (s, 1H), 7.81 (m, 1H), 7.51 (m, 1H), 7.36 (br s, 2H), 3.76 (s, 3H); IR (neat film) 3479 (s), 3409 (s), 3286 (m), 3159 (m), 2955 (w), 2853 (w), 1690 (s), 1639 (s) cm$^{-1}$; ESIMS m/z 328.9 ([M−H]$^−$).

Example 12

Preparation of sodium 2-propenyloxy(4-amino-3-chloro-6-(4-chloro-2-fluoro-3-methoxyphenyl)picolinoyl)amide (Compound 59)

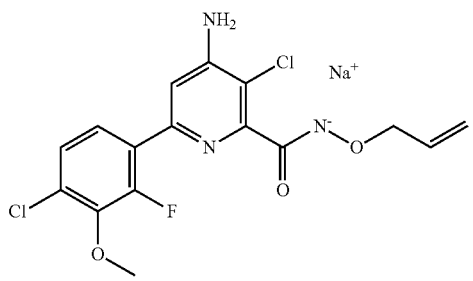 [SMILES: C=CCO[N-]C(=O)c1nc(-c2ccc(Cl)c(OC)c2F)cc(N)c1Cl ; [Na+]]

NaH (60% dispersion in mineral oil; 33 mg, 0.82 mmol, 1.05 equiv) was added to a stirred solution of N-(allyloxy)-4-amino-3-chloro-6-(4-chloro-2-fluoro-3-methoxy-phenyl) picolinamide (300 mg, 0.78 mmol, 1.0 equiv) in THF (7.8 mL) at 23° C. The vigorously bubbling off-white mixture was stirred at 23° C. for 1 h. The resulting homogeneous light tan solution was concentrated via rotary evaporation. The residue was slurried in hexane and vacuum filtered to afford an off-white powder (260 mg, 81%): mp 236-240° C. dec; $^1$H NMR (300 MHz, DMSO-$d_6$) δ 7.59 (dd, J=9, 8 Hz, 1H), 7.34 (dd, J=9, 2 Hz, 1H), 7.00 (d, J=2 Hz, 1H), 6.18 (br s, 2H), 6.01 (m, 1H), 5.18 (m, 1H), 5.03 (m, 1H), 4.13 (m, 2H), 3.92 (d, J=1 Hz, 3H).

Example 13

Evaluation of General Postemergence Herbicidal Activity

Seeds or nutlets of the desired test plant species were planted in Sun Gro MetroMix® 360 planting mixture, which typically has a pH of 6.0 to 6.8 and an organic matter content of about 30 percent, in plastic pots with a surface area of 64 square centimeters (cm$^2$). When required to ensure good germination and healthy plants, a fungicide treatment and/or other chemical or physical treatment was applied. The plants were grown for 7-21 days (d) in a greenhouse with an approximate 15-hour (h) photoperiod which was maintained at about 23-29° C. during the day and 22-28° C. during the night. Nutrients and water were added on a regular basis and supplemental lighting was provided with overhead metal halide 1000-Watt lamps as necessary. The plants were employed for testing when they reached the first or second true leaf stage.

A weighed amount, determined by the highest rate to be tested, of each test compound was dissolved in 4 mL of a 97:3 volume per volume (v/v) mixture of acetone and dimethyl sulfoxide (DMSO) to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain spray solutions containing the highest application rates. Additional application rates were obtained by serial dilution of 12 mL of the high rate solution into a solution containing 2 mL of 97:3 v/v mixture of acetone and DMSO and 10 mL of an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain ½×, ¼×, ⅛× and 1/16× rates of the high rate. Compound requirements are based upon a 12 mL application volume at a rate of 187 liters per hectare (L/ha). Formulated compounds were applied to the plant material with an overhead Mandel track sprayer equipped with 8002E nozzles calibrated to deliver 187 L/ha over an application area of 0.503 square meters (m$^2$) at a spray height of 18 inches (43 cm) above the average plant canopy height. Control plants were sprayed in the same manner with the solvent blank.

The treated plants and control plants were placed in a greenhouse as described above and watered by sub-irrigation to prevent wash-off of the test compounds. After 14 d, the condition of the test plants as compared with that of the untreated plants was determined visually and scored on a scale of 0 to 100 percent where 0 corresponds to no injury and 100 corresponds to complete kill.

Some of the compounds tested, application rates employed, plant species tested, and results are given in Table 1.

TABLE 1

| | | Post-emergent Herbicidal Activity | | | |
|---|---|---|---|---|---|
| Compound | Rate (g ai/ha) | ZEAMX | ABUTH | CHEAL | POLCO |
| | | % Visual Injury | | | |
| 1 | 70 | 0 | 100 | 100 | 100 |
| 2 | 70 | 10 | 100 | 100 | 100 |
| 3 | 140 | 0 | 100 | 100 | 100 |
| 4 | 140 | 0 | 100 | 100 | 100 |
| 5 | 35 | 0 | 100 | 100 | 100 |
| 6 | 70 | 0 | 100 | 100 | 100 |
| 7 | 35 | 25 | 100 | 100 | 100 |
| 8 | 70 | 0 | 100 | 100 | 100 |
| 9 | 140 | 25 | 95 | 100 | 80 |
| 10 | 140 | 15 | 100 | 85 | 15 |
| 11 | 140 | 20 | 40 | 100 | 100 |
| 12 | 70 | 0 | 100 | 100 | 100 |

TABLE 1-continued

Post-emergent Herbicidal Activity

| Compound | Rate (g ai/ha) | ZEAMX | ABUTH | CHEAL | POLCO |
|---|---|---|---|---|---|
| | | | % Visual Injury | | |
| 13 | 70 | 0 | 100 | 100 | 100 |
| 14 | 70 | 15 | 100 | 100 | 100 |
| 15 | 70 | 10 | 100 | 100 | 100 |
| 16 | 70 | 10 | 100 | 100 | 95 |
| 17 | 70 | 10 | 100 | 100 | 100 |
| 18 | 140 | 5 | 100 | 100 | 100 |
| 19 | 35 | 25 | 85 | 100 | 85 |
| 20 | 70 | 25 | 100 | 95 | 100 |
| 21 | 140 | 0 | 100 | 95 | 95 |
| 22 | 35 | 10 | 100 | 100 | 100 |
| 23 | 70 | 15 | 100 | 100 | 100 |
| 24 | 70 | 50 | 90 | 95 | 80 |
| 25 | 8.75 | 60 | 90 | 100 | 100 |
| 26 | 140 | 0 | 95 | 100 | 95 |
| 27 | 280 | 0 | 35 | 100 | 100 |
| 28 | 35 | 25 | 100 | 100 | NT |
| 29 | 35 | 50 | 100 | 100 | 100 |
| 30 | 70 | 50 | 100 | 100 | 100 |
| 31 | 70 | 5 | 100 | 100 | 100 |
| 32 | 35 | 10 | 100 | 100 | 100 |
| 33 | 70 | 10 | 100 | 100 | 100 |
| 34 | 280 | 20 | 65 | 100 | 100 |
| 35 | 140 | 20 | 100 | 100 | 90 |
| 36 | 35 | 25 | 100 | 100 | NT |
| 37 | 17.5 | 25 | 100 | 100 | 100 |
| 38 | 35 | 35 | 100 | 100 | 100 |
| 39 | 17.5 | 45 | 100 | 100 | 100 |
| 40 | 140 | 20 | 95 | 100 | 100 |
| 41 | 70 | 5 | 100 | 100 | 100 |
| 42 | 70 | 15 | 100 | 100 | 100 |
| 43 | 140 | 30 | 95 | 100 | 100 |
| 44 | 140 | 5 | 98 | 98 | 100 |
| 45 | 140 | 30 | 100 | 100 | 100 |
| 46 | 70 | 25 | 100 | 100 | 100 |
| 47 | 17.5 | 35 | 100 | 100 | NT |
| 48 | 140 | 0 | 100 | 100 | 100 |
| 49 | 280 | 0 | 100 | 100 | 100 |
| 50 | 280 | 10 | 100 | 100 | 90 |
| 51 | 35 | 35 | 100 | 100 | 100 |
| 52 | 35 | 20 | 100 | 90 | 100 |
| 57 | 17.5 | 0 | 90 | 95 | 95 |
| 58 | 280 | 0 | 90 | 100 | 100 |
| 59 | 70 | 10 | 100 | 95 | 85 |

NT = Not Tested
ZEAMX = corn (*Zea mays*)
CHEAL = lambsquarters (*Chenopodium album*)
ABUTH = velvetleaf (*Abutilon theophrasti*)
POLCO = wild buckwheat (*Polygonum convulvulus*)
g ai/ha = grams of active ingredient per hectare

Example 14

Evaluation of Postemergence Herbicidal Activity in Corn

Seeds of corn and the desired weed species were planted in Sun Gro MetroMix® 360 planting mixture, which typically has a pH of 6.0 to 6.8 and an organic matter content of about 30 percent, in plastic pots with a surface area of 95 cm². When required to ensure good germination and healthy plants, a fungicide treatment and/or other chemical or physical treatment was applied. The plants were grown for 7-21 d in a greenhouse with an approximate 15-h photoperiod which was maintained at about 23-29° C. during the day and 22-28° C. during the night. Nutrients and water were added on a regular basis and supplemental lighting was provided with overhead metal halide 1000-Watt lamps as necessary. The corn plants were utilized for testing when they reached the second true leaf stage. The weed species were utilized at the first or second true leaf stage.

A weighed amount, determined by the highest rate to be tested, of each test compound was dissolved in 4 mL of a 97:3 v/v mixture of acetone and DMSO to obtain concentrated stock solutions. If the test compound did not dissolve readily, the mixture was warmed and/or sonicated. The concentrated stock solutions obtained were diluted with 20 mL of an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain spray solutions containing the highest application rates. Additional application rates were obtained by serial dilution of 12 mL of the high rate solution into a solution containing 2 mL of 97:3 v/v mixture of acetone and DMSO and 10 mL of an aqueous mixture containing acetone, water, isopropyl alcohol, DMSO, Atplus 411F crop oil concentrate, and Triton X-155 surfactant in a 48.5:39:10:1.5:1.0:0.02 v/v ratio to obtain ½×, ¼×, ⅛× and 1/16× rates of the high rate. Compound requirements are based upon a 12 mL application volume at a rate of 187 L/ha. Formulated compounds were applied to the plant material with an overhead Mandel track sprayer equipped with 8002E nozzles calibrated to deliver 187 L/ha over an application area of 0.503 m² at a spray height of 18 inches (43 cm) above the average plant canopy height. Control plants were sprayed in the same manner with the solvent blank.

The treated plants and control plants were placed in a greenhouse as described above and watered by sub-irrigation to prevent wash-off of the test compounds. After 21 d, the condition of the test plants as compared with that of the untreated plants was determined visually and scored on a scale of 0 to 100 percent where 0 corresponds to no injury and 100 corresponds to complete kill.

By applying the well-accepted probit analysis as described by J. Berkson in *Journal of the American Statistical Society* 1953, 48, 565, and by D. Finney in "*Probit Analysis*" Cambridge University Press (1952), the above data can be used to calculate $GR_{20}$ and $GR_{80}$ values, which are defined as growth reduction factors that correspond to the effective dose of herbicide required to kill or control 20 percent or 80 percent, respectively, of a target plant.

Some of the compounds tested, plant species tested, and results are given in Table 2.

TABLE 2

Post-emergent Herbicidal Activity in Corn

| Compound | ZEAMX $GR_{20}$ (g ai/ha) | CASOB | POLCO $GR_{80}$ (g ai/ha) | AMARE | CHEAL |
|---|---|---|---|---|---|
| 1 | >35 | 8.75 | <4 | 14 | <4 |
| 2 | >35 | 17 | 6 | <4 | <4 |
| 3 | >35 | 5 | <4 | 5 | <4 |

ZEAMX = corn (*Zea mays*)
CASOB = sicklepod (*Casia obtusifolia*)
POLCO = wild buckwheat (*Polygonum convulvulus*)
AMARE = pigweed, redroot (*Amaranthus retroflexus*)
CHEAL = lambsquarters (*Chenopodium album*)

Example 15

Evaluation of Postemergence Herbicidal Activity in Sugar Beet

Seeds of sugar beet and the desired weed species were planted in Sun Gro MetroMix® 360 planting mixture, which typically has a pH of 6.0 to 6.8 and an organic matter content of about 30 percent, in plastic pots with a surface area of 95 cm². When required to ensure good germination and healthy plants, a fungicide treatment and/or other chemical or physical treatment was applied. The plants were grown for 15-28 d in a greenhouse with an approximate 15-h photoperiod which was maintained at about 23-29° C. during the day and 22-28° C. during the night. Nutrients and water were added on a regular basis and supplemental lighting was provided with overhead metal halide 1000-Watt lamps as necessary. The sugar beet plants were utilized for testing when they reached the third or fourth true leaf stage. The weed species were utilized at the fourth true leaf stage.

A weighed amount, determined by the highest rate to be tested, of each test compound was dissolved in 4 mL of a 97:3 v/v mixture of acetone and DMSO to obtain concentrated stock solutions. If the test compound did not dissolve readily, the mixture was warmed and/or sonicated. The concentrated stock solutions obtained were diluted with 20 mL of an aqueous mixture containing acetone, water and Agri-Dex crop oil concentrate, in a 16.7:82.1:1.25 v/v ratio to obtain spray solutions containing the highest application rates. Additional application rates were obtained by serial dilution of 12 mL of the high rate solution into a solution containing 2 mL of 97:3 v/v mixture of acetone and DMSO and 10 mL of an aqueous mixture containing acetone, water and Agri-Dex crop oil concentrate, in a 16.7:82.1:1.25 v/v ratio to obtain ½×, ¼×, ⅛× and 1/16× rates of the high rate. Compound requirements are based upon a 12 mL application volume at a rate of 187 L/ha. Formulated compounds were applied to the plant material with an overhead Mandel track sprayer equipped with 8002E nozzles calibrated to deliver 187 L/ha over an application area of 0.503 m² at a spray height of 18 inches (43 cm) above the average plant canopy height. Control plants were sprayed in the same manner with the solvent blank.

The treated plants and control plants were placed in a greenhouse as described above and watered by sub-irrigation to prevent wash-off of the test compounds. After 21 d, the condition of the test plants as compared with that of the untreated plants was determined visually and scored on a scale of 0 to 100 percent where 0 corresponds to no injury and 100 corresponds to complete kill.

By applying the well-accepted probit analysis as described by J. Berkson in *Journal of the American Statistical Society* 1953, 48, 565, and by D. Finney in "*Probit Analysis*" Cambridge University Press (1952), the above data can be used to calculate $GR_{20}$ and $GR_{80}$ values, which are defined as growth reduction factors that correspond to the effective dose of herbicide required to kill or control 20 percent or 80 percent, respectively, of a target plant.

Some of the compounds tested, plant species tested, and results are given in Table 3.

TABLE 3

Post-emergent Herbicidal Activity in Sugar beet

| Compound | BEAVA $GR_{20}$ | CHEAL | LAMPU $GR_{80}$ |
|---|---|---|---|
| 2 | >35 | 21.5 | <4.38 |
| 4 | >140 | <8.75 | <4.38 |
| 30 | >140 | <8.75 | <4.38 |
| 31 | >140 | <8.75 | NT |
| 41 | 136 | 30 | <4.38 |

BEAVA = sugar beet (*Beta vulgaris*)
CHEAL = lambsquarters (*Chenopodium album*)
LAMPU = purple deadnettle (*Lamium purpureum*)

Example 16

Evaluation of Postemergence Herbicidal Activity in Oilseed Rape (Canola)

Seeds of oilseed rape (canola) and the desired weed species were planted in Sun Gro MetroMix® 360 planting mixture, which typically has a pH of 6.0 to 6.8 and an organic matter content of about 30 percent, in plastic pots with a surface area of 95 cm². When required to ensure good germination and healthy plants, a fungicide treatment and/or other chemical or physical treatment was applied. The plants were grown for 15-28 d in a greenhouse with an approximate 15-h photoperiod which was maintained at about 23-29° C. during the day and 22-28° C. during the night. Nutrients and water were added on a regular basis and supplemental lighting was provided with overhead metal halide 1000-Watt lamps as necessary. The oilseed rape (canola) plants were utilized for testing when they reached the third or fourth true leaf stage. The weed species were utilized at the fourth true leaf stage.

A weighed amount, determined by the highest rate to be tested, of each test compound was dissolved in 4 mL of a 97:3 v/v mixture of acetone and DMSO to obtain concentrated stock solutions. If the test compound did not dissolve readily, the mixture was warmed and/or sonicated. The concentrated stock solutions obtained were diluted with 20 mL of an aqueous mixture containing acetone, water and Agri-Dex crop oil concentrate, in a 16.7:82.1:1.25 v/v ratio to obtain spray solutions containing the highest application rates. Additional application rates were obtained by serial dilution of 12 mL of the high rate solution into a solution containing 2 mL of 97:3 v/v mixture of acetone and DMSO and 10 mL of an aqueous mixture containing acetone, water and Agri-Dex crop oil concentrate, in a 16.7:82.1:1.25 v/v ratio to obtain ½×, ¼×, ⅛× and 1/16× rates of the high rate. Compound requirements are based upon a 12 mL application volume at a rate of 187 L/ha. Formulated compounds were applied to the plant material with an overhead Mandel track sprayer equipped with 8002E nozzles calibrated to deliver 187 L/ha over an application area of 0.503 m² at a spray height of 18 inches (43 cm) above the average plant canopy height. Control plants were sprayed in the same manner with the solvent blank.

The treated plants and control plants were placed in a greenhouse as described above and watered by sub-irrigation to prevent wash-off of the test compounds. After 21 d, the condition of the test plants as compared with that of the untreated plants was determined visually and scored on a scale of 0 to 100 percent where 0 corresponds to no injury and 100 corresponds to complete kill.

By applying the well-accepted probit analysis as described by J. Berkson in *Journal of the American Statistical Society* 1953, 48, 565, and by D. Finney in "*Probit Analysis*" Cambridge University Press (1952), the above data can be used to calculate $GR_{20}$ and $GR_{80}$ values, which are defined as growth reduction factors that correspond to the effective dose of herbicide required to kill or control 20 percent or 80 percent, respectively, of a target plant.

Some of the compounds tested, plant species tested, and results are given in Table 4.

TABLE 4

Post-emergent Herbicidal Activity in Oilseed Rape (Canola)

| Compound | BRSNW $GR_{20}$ | CHEAL | LAMPU $GR_{80}$ |
|---|---|---|---|
| 2 | >70 | 22 | <4.38 |
| 4 | >140 | 11 | <4.38 |
| 1 | >70 | <8.75 | <4.38 |
| 30 | >70 | <8.75 | <4.38 |
| 39 | >70 | 49 | <8.75 |
| 48 | >70 | 18 | <4.38 |

BRSNW = winter oilseed rape (canola) (*Brassica napus*)
CHEAL = lambsquarters (*Chenopodium album*)
LAMPU = purple deadnettle (*Lamium purpureum*)

What is claimed is:

1. An herbicidal composition comprising an herbicidally effective amount of a compound of Formula I, wherein
X represents CH, CF, or N;
Y represents phenyl substituted with 1-4 substituents independently selected from halogen, $C_1$-$C_3$ alkyl, $C_3$-$C_6$ cycloalkyl, $C_1$-$C_3$ alkoxy, $C_1$-$C_3$ haloalkyl, $C_1$-$C_3$ haloalkoxy, cyano, nitro, $N(R^4)_2$, or where two adjacent substituents are taken together as —OCH$_2$O—;
Z represents halogen, $C_1$-$C_3$ alkoxy, or $C_2$-$C_4$ alkenyl;
$R^1$ represents H, $C_1$-$C_3$ alkyl, $C_2$-$C_4$ acyl, or benzyl;
$R^2$ represents H, $C_1$-$C_3$ alkyl, or $C_2$-$C_4$ acyl;
$R^3$ represents H, $C_1$-$C_8$ alkyl, $C_3$-$C_8$ cycloalkyl, haloalkyl, alkoxyalkyl, cyanoalkyl, alkylcarbonyl, alkylthio, alkylsulfonyl, $C_2$-$C_8$ alkenyl, $C_5$-$C_8$ cycloalkenyl, haloalkenyl, $C_2$-$C_8$ alkynyl, unsubstituted or substituted phenyl, unsubstituted or substituted heteroaryl, unsubstituted or substituted heterocyclyl, alkylcycloalkyl, alkylcycloalkenyl, unsubstituted or substituted arylalkyl, or $R^2$ and $R^3$ together with the O and N atoms to which they are joined form an unsubstituted or substituted 5- to 7-membered ring optionally containing one further heteroatom selected from O, N, and S; and
$R^4$ represents H or $C_1$-$C_3$ alkyl;
or a salt thereof; in a mixture with an agriculturally acceptable adjuvant or carrier.

2. A method for postemergent control of undesirable vegetation which comprises applying to said undesirable vegetation an herbicidally effective amount of a compound of Formula I, wherein
X represents CH, CF, or N;
Y represents phenyl substituted with 1-4 substituents independently selected from halogen, $C_1$-$C_3$ alkyl, $C_3$-$C_6$ cycloalkyl, $C_1$-$C_3$ alkoxy, $C_1$-$C_3$ haloalkyl, $C_1$-$C_3$ haloalkoxy, cyano, nitro, $N(R^4)_2$, or where two adjacent substituents are taken together as —OCH$_2$O—;
Z represents halogen, $C_1$-$C_3$ alkoxy, or $C_2$-$C_4$ alkenyl;
$R^1$ represents H, $C_1$-$C_3$ alkyl, $C_2$-$C_4$ acyl, or benzyl;
$R^2$ represents H, $C_1$-$C_3$ alkyl, or $C_2$-$C_4$ acyl;
$R^3$ represents H, $C_1$-$C_8$ alkyl, $C_3$-$C_8$ cycloalkyl, haloalkyl, alkoxyalkyl, cyanoalkyl, alkylcarbonyl, alkylthio, alkylsulfonyl, $C_2$-$C_8$ alkenyl, $C_5$-$C_8$ cycloalkenyl, haloalkenyl, $C_2$-$C_8$ alkynyl, unsubstituted or substituted phenyl, unsubstituted or substituted heteroaryl, unsubstituted or substituted heterocyclyl, alkylcycloalkyl, alkylcycloalkenyl, unsubstituted or substituted arylalkyl, or $R^2$ and $R^3$ together with the O and N atoms to which they are joined form an unsubstituted or substituted 5- to 7-membered ring optionally containing one further heteroatom selected from O, N, and S; and
$R^4$ represents H or $C_1$-$C_3$ alkyl;
or a salt thereof;
or an herbicidal composition thereof.

3. The method of claim 2 wherein the compound of Formula I is applied to said undesirable vegetation in the presence of corn; said undesirable vegetation comprises lambsquarters (*Chenopodium album*), velvetleaf (*Abutilon theophrasti*), wild buckwheat (*Polygonum convululus*), sicklepod (*Casia obtusifolia*), or pigweed, redroot (*Amaranthus retroflexus*).

4. The method of claim 3 wherein the compound of Formula I is selected from the group consisting of:
4-amino-3-chloro-6-(4-chloro-2-fluoro-3-methoxyphenyl)-N-(2-methylpropoxy)picolinamide (Compound 1),
4-Amino-3-chloro-6-(4-chloro-2-fluoro-3-methoxyphenyl)-N-methoxypicolinamide (Compound 2),
N-(2-Propenyloxy)-4-amino-3-chloro-6-(4-chloro-2-fluoro-3-methoxyphenyl)picolinamide (Compound 3),
4-Amino-3-chloro-6-(4-chloro-2-fluoro-3-methoxyphenyl)-N-ethoxypicolinamide (Compound 4),
4-Amino-N-(benzyloxy)-3-chloro-6-(4-chloro-2-fluoro-3-methoxyphenyl)picolinamide (Compound 5),
4-Amino-3-chloro-6-(4-chloro-2-fluoro-3-methoxyphenyl)-N-methoxy-N-methyl-picolinamide (Compound 6),
4-Amino-3-chloro-6-(4-chloro-2-fluoro-3-methoxyphenyl)-N-propoxypicolinamide (Compound 7),
4-Amino-3-chloro-6-(4-chloro-2-fluoro-3-methoxyphenyl)-N-isopropoxypicolinamide (Compound 8),
N-Acetyl-N-(2-propenyloxy)-6-amino-2-(4-chloro-2-fluoro-3-methoxyphenyl)-5-vinylpyrimidine-4-carboxamide (Compound 9), N-(2-Propenyloxy)-6-amino-2-(4-chloro-2-fluoro-3-methoxyphenyl)-5-vinylpyrimidine-4-carboxamide (Compound 10),
N-(2-Propenyloxy)-6-amino-5-chloro-2-cyclopropylpyrimidine-4-carboxamide (Compound 11),
4-amino-3-chloro-6-(4-chloro-2-fluoro-3-methoxyphenyl)-N-(tetrahydro-2H-pyran-2-yloxy)picolinamide (Compound 12),
4-Amino-3-chloro-6-(4-chloro-2-fluoro-3-methoxyphenyl)-N-(2-propynyloxy)picolinamide (Compound 13),
4-Amino-3-chloro-6-(4-chloro-2-fluoro-3-methoxyphenyl)-N-(4-methyl-benzyloxy)picolinamide (Compound 14),
4-Amino-3-chloro-6-(4-chloro-2-fluoro-3-methoxyphenyl)-N-(4-chloro-benzyloxy)picolinamide (Compound 15),
4-Amino-3-chloro-6-(4-chloro-2-fluoro-3-methoxyphenyl)-N-((2R,3R,4S,5R,6R)-3,4,5-trimethoxy-6-(methoxymethyl)tetrahydro-2H-pyran-2-yloxy)picolinamide (Compound 16),
4-Amino-3-chloro-6-(4-chloro-2-fluoro-3-methoxyphenyl)-N-(tetrahydrofuran-2-yloxy)picolinamide (Compound 17),
4-Amino-3-chloro-6-(4-chloro-2-fluoro-3-methoxyphenyl)-N-(cyclohex-2-enyl-oxy)picolinamide (Compound 18),
2-(4-Amino-3-chloro-6-(4-chloro-2-fluoro-3-methoxyphenyl)picolinamidooxy)acetic acid (Compound 19),
4-Amino-3-chloro-6-(4-chloro-2-fluoro-3-methoxyphenyl)-N-phenoxypicolinamide (Compound 20),
4-Amino-N-tert-butoxy-3-chloro-6-(4-chloro-2-fluoro-3-methoxyphenyl)picolinamide (Compound 21),
4-Amino-3-chloro-6-(4-chloro-2-fluoro-3-methoxyphenyl)-N-(4-fluoro-benzyloxy)picolinamide (Compound 22),
4-Amino-3-chloro-6-(4-chloro-2-fluoro-3-methoxyphenyl)-N-(4-methoxy-benzyloxy)picolinamide (Compound 23),
4-Amino-3-chloro-6-(4-chloro-2-fluoro-3-methoxyphenyl)-N-hydroxy-N-methylpicolinamide (Compound 24),
N-(2-Propenyloxy)-6-amino-5-chloro-2-(4-chloro-2-fluoro-3-methoxyphenyl)pyrimidine-4-carboxamide (Compound 25),
N-(2-Propenyloxy)-4-amino-3-chloro-6-(4-chloro-2-fluoro-3-methoxyphenyl)-N-methylpicolinamide (Compound 26),
N-(2-Propenyloxy)-4-amino-3,6-dichloropicolinamide (Compound 27),
4-Amino-3-chloro-6-(4-chloro-2-fluoro-3-methoxyphenyl)-N-(2-methyl-2-propenyl-oxy)picolinamide (Compound 28),
4-Amino-3-chloro-6-(4-chloro-2-fluoro-3-methoxyphenyl)-N-(2-chloro-2-propenyl-oxy)picolinamide (Compound 29),
(E)-4-Amino-N-(2-butenyloxy)-3-chloro-6-(4-chloro-2-fluoro-3-methoxy-phenyl)picolinamide (Compound 30),
(E)-4-Amino-3-chloro-6-(4-chloro-2-fluoro-3-methoxyphenyl)-N-(3-chloro-2-propenyl-oxy)picolinamide (Compound 31),
4-Amino-3-chloro-6-(4-chloro-2-fluoro-3-methoxyphenyl)-N-(cyclopropyl-methoxy)picolinamide (Compound 32),
4-Amino-N-(but-3-en-2-yloxy)-3-chloro-6-(4-chloro-2-fluoro-3-methoxy-phenyl)picolinamide (Compound 33),
4-Amino-3,6-dichloro-N-(4-fluorobenzyloxy)picolinamide (Compound 34),
N-(2-Propenyloxy)-6-amino-2-(4-chloro-2-fluoro-3-methoxyphenyl)-5-methoxypyrimidine-4-carboxamide (Compound 35),
4-Amino-3-chloro-6-(4-chloro-2-fluoro-3-methoxyphenyl)-N-(thiazol-5-yl-methoxy)picolinamide (Compound 36),
4-Amino-3-chloro-6-(4-chloro-2-fluoro-3-methoxyphenyl)-N-(2-fluoro-2-propenyl-oxy)picolinamide (Compound 37),
4-Amino-N-(3-butenyloxy)-3-chloro-6-(4-chloro-2-fluoro-3-methoxyphenyl)picolinamide (Compound 38),
N-(2-Propenyloxy)-4-amino-3-chloro-6-(4-chloro-2-fluoro-3-methoxyphenyl)-5-fluoropicolinamide (Compound 39),
(4-Amino-3-chloro-6-(4-chloro-2-fluoro-3-methoxyphenyl)pyridin-2-yl)(isoxazolidin-2-yl)methanone (Compound 40),
4-Amino-3-chloro-6-(4-chloro-2-fluoro-3-methoxyphenyl)-N-((2-chlorothiazol-5-yl)-methoxy)picolinamide (Compound 41),
4-Amino-3-chloro-6-(4-chloro-2-fluoro-3-methoxyphenyl)-N-(furan-2-yl-methoxy)picolinamide (Compound 42),
4-Amino-3-chloro-6-(4-chloro-2-fluoro-3-methoxyphenyl)-N-(furan-3-yl-methoxy)picolinamide (Compound 43),
4-Amino-3-chloro-6-(4-chloro-2-fluoro-3-methoxyphenyl)-N-(cyclohexenyl-methoxy)picolinamide (Compound 44),
(E)-4-Amino-3-chloro-6-(4-chloro-2-fluoro-3-methoxyphenyl)-N-(2-pentenyl-oxy)picolinamide (Compound 45),
4-Amino-N-butoxy-3-chloro-6-(4-chloro-2-fluoro-3-methoxyphenyl)picolinamide (Compound 46),
4-Amino-3-chloro-N-((5-chloro-1,2,3-thiadiazol-4-yl)methoxy)-6-(4-chloro-2-fluoro-3-methoxyphenyl)picolinamide (Compound 47),
4-Amino-3-chloro-6-(4-chloro-2-fluoro-3-methoxyphenyl)-5-fluoro-N-(tetrahydro-2H-pyran-2-yloxy)picolinamide (Compound 48),
4-Amino-3-chloro-6-(4-chloro-2-fluoro-3-methoxyphenyl)-N-(2-methoxy-ethoxy)picolinamide (Compound 49),
4-Amino-3-chloro-6-(4-chloro-2-fluoro-3-methoxyphenyl)-N-(2-cyanoethoxy)picolinamide (Compound 50),
4-Amino-3-chloro-6-(4-chloro-2-fluoro-3-methoxyphenyl)-N-((2-methoxyethoxy)-methoxy)picolinamide (Compound 51),
(4-Amino-3-chloro-6-(4-chloro-2-fluoro-3-methoxyphenyl)pyridin-2-yl)(3,6-dihydro-2H-1,2-oxazin-2-yl)methanone (Compound 52),
N-(2-Propenyloxy)-4-amino-3-chloro-6-(4-methylphenyl)picolinamide (Compound 53),
N-(2-Propenyloxy)-4-amino-3-chloro-6-(benzo[d][1,3]dioxol-5-yl)-3-chloropicolinamide (Compound 54),
N-(2-Propenyloxy)-4-amino-3-chloro-6-(4-fluorophenyl)picolinamide (Compound 55),
N-(2-Propenyloxy)-4-amino-3-chloro-6-(4-cyanophenyl)picolinamide (Compound 56),
4-amino-3-chloro-6-(4-chloro-2-fluoro-3-methoxyphenyl)-N-hydroxypicolinamide (Compound 57),
6-Amino-2-(4-chloro-2,3-difluorophenyl)-N-hydroxy-5-methoxypyrimidine-4-carboxamide (Compound 58), and sodium 2-propenyloxy(4-amino-3-chloro-6-(4-chloro-2-fluoro-3-methoxyphenyl)picolinoyl)amide (Compound 59).

5. The method of claim 2 wherein the compound of Formula I is applied to said undesirable vegetation in the presence of sugar beet; said undesirable vegetation comprises lambsquarters (*Chenopodium album*) or purple deadnettle (*Lamium purpureum*).

6. The method of claim 5 wherein the compound of Formula I is selected from the group consisting of
- 4-Amino-3-chloro-6-(4-chloro-2-fluoro-3-methoxyphenyl)-N-methoxypicolinamide (Compound 2),
- 4-Amino-3-chloro-6-(4-chloro-2-fluoro-3-methoxyphenyl)-N-ethoxypicolinamide (Compound 4),
- (E)-4-Amino-N-(2-butenyloxy)-3-chloro-6-(4-chloro-2-fluoro-3-methoxy-phenyl)picolinamide (Compound 30),
- (E)-4-Amino-3-chloro-6-(4-chloro-2-fluoro-3-methoxyphenyl)-N-(3-chloro-2-propenyl-oxy)picolinamide (Compound 31), and
- 4-Amino-3-chloro-6-(4-chloro-2-fluoro-3-methoxyphenyl)-N-((2-chlorothiazol-5-yl)-methoxy)picolinamide (Compound 41).

7. The method of claim 2 wherein the compound of Formula I is applied to said undesirable vegetation in the presence of oilseed rape; and said undesirable vegetation comprises lambsquarters (*Chenopodium album*) or purple deadnettle (*Lamium purpureum*).

8. The method of claim 7 wherein the compound of Formula I is selected from the group consisting of:
- 4-amino-3-chloro-6-(4-chloro-2-fluoro-3-methoxyphenyl)-N-(2-methylpropoxy)picolinamide (Compound 1),
- 4-Amino-3-chloro-6-(4-chloro-2-fluoro-3-methoxyphenyl)-N-methoxypicolinamide (Compound 2),
- 4-Amino-3-chloro-6-(4-chloro-2-fluoro-3-methoxyphenyl)-N-ethoxypicolinamide (Compound 4),
- (E)-4-Amino-N-(2-butenyloxy)-3-chloro-6-(4-chloro-2-fluoro-3-methoxy-phenyl)picolinamide (Compound 30),
- N-(2-Propenyloxy)-4-amino-3-chloro-6-(4-chloro-2-fluoro-3-methoxyphenyl)-5-fluoropicolinamide (Compound 39), and
- 4-Amino-3-chloro-6-(4-chloro-2-fluoro-3-methoxyphenyl)-5-fluoro-N-(tetrahydro-2H-pyran-2-yloxy)picolinamide (Compound 48).

* * * * *